(12) United States Patent
Nagasaka et al.

(10) Patent No.: US 8,673,563 B2
(45) Date of Patent: Mar. 18, 2014

(54) AMPLIFICATION METHOD OF METHYLATED OR UNMETHYLATED NUCLEIC ACID

(75) Inventors: Takeshi Nagasaka, Okayama (JP);
Nagahide Matsubara, Hyogo (JP);
Hiromi Sasamoto, Okayama (JP);
Noriaki Tanaka, Okayama (JP)

(73) Assignee: Bio-Dixam, LLC (JP)

( * ) Notice: Subject to any disclaimer, the term of this patent is extended or adjusted under 35 U.S.C. 154(b) by 880 days.

(21) Appl. No.: 12/602,094

(22) PCT Filed: Jun. 3, 2008

(86) PCT No.: PCT/JP2008/060205
§ 371 (c)(1),
(2), (4) Date: Mar. 17, 2010

(87) PCT Pub. No.: WO2008/149855
PCT Pub. Date: Dec. 11, 2008

(65) Prior Publication Data
US 2011/0097714 A1 Apr. 28, 2011

(30) Foreign Application Priority Data
Jun. 8, 2007 (JP) ................. 2007-153086

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC ....... 435/6.11; 435/6.12; 435/91.2; 536/23.1; 536/24.3

(58) Field of Classification Search
None
See application file for complete search history.

(56) References Cited

U.S. PATENT DOCUMENTS

2003/0170649 A1* 9/2003 Haas et al. .......... 435/6

FOREIGN PATENT DOCUMENTS

| JP | 2000-511776 | 9/2000 |
|---|---|---|
| JP | 2007-74950 | 3/2007 |
| WO | 9746705 | 12/1997 |
| WO | WO 02/38801 A1 | 5/2002 |
| WO | WO 2008/011620 A2 * | 1/2008 |
| WO | WO 2008/149855 | 12/2008 |

OTHER PUBLICATIONS

Herman, J.G. et al., PNAS USA, vol. 93, pp. 9821-9826 (1996).*
Thomassin, H. et al., Nucl. Acids res., vol. 32, e168, pp. 1-9 (2004).*
Buck, G.A. et al., Biotechniques, vol. 27, pp. 528-536 (1999).*
Ylitalo, N. et al., J. Clin. Microbiol., vol. 33, pp. 1822-1828 (1995).*
Hesson, L.B. et al., Oncogene, vol. 24, pp. 3987-3994 (2005).*
Zhang, Z. et al., Int. J. Cancer, vol. 120, pp. 32-38 (Sep. 2006).*
Li, L-C. et al., Bioinformatics, vol. 18, pp. 1427-1431 (2002).*
Nagasaka et al., Acta Med. Okayama, 2006, vol. 60. No. 5, p. 249-256.
Xiong Z, Laird PW. Nucleic Acids Res. Jun. 15, 1997;25(12): 2532-4.
Beatty, L. et al. "Detailed analysis of the methylation patterns of the KvDMR1 imprinting control region of human chromosome 11." Genomics, Academic Press, San Diego, LNKD- DOI:10.1016/J.YGENO.2005.05.015. vol. 87, No. 1, Jan. 1, 2006, pp. 46-56.
Dahl, Christina et al. "DNA methylation analysis techniques." Biogerontology, Kluwer Academic Publishers, DO LNKD-DOI:10.1023/A:1025103319328, vol. 4, No. 4, Aug. 1, 2003, pp. 233-250.
Kato, Keizo et al. "Aberrant promoter hypermethylation of p16 and MGMT genes in oral squamous cell carcinomas and the surrounding normal mucosa." Journal of Cancer Research and Clinical Oncology, Springer, Berlin, DE LNKD-DOI:10.1007/S00432-006-0122-8, vol. 132, No. 11, Jun. 22, 2006, whole document.

* cited by examiner

*Primary Examiner* — Teresa E Strzelecka
(74) *Attorney, Agent, or Firm* — Marianne Fuierer; Moore & Van Allen, PLLC

(57) ABSTRACT

The object of the present invention is to provide a gene amplification method, wherein the method can amplify both methylated and unmethylated nucleic acids present in a biological sample, and further regulate the amplification ratio of the methylated and/or unmethylated nucleic acid as needed. Such objects can be solved by an amplification method using a nonspecific primer which can hybridize both with methylated and unmethylated nucleic acids and a specific primer which specifically hybridizes with either methylated or unmethylated nucleic acid, and further by an amplification method which can change the amplification ratio of methylated or unmethylated nucleic acid by changing the mixing rate of these primers.

15 Claims, 10 Drawing Sheets

AMPLIFICATION METHOD OF METHYLATED OR UNMETHYLATED NUCLEIC ACID

TECHNICAL FIELD

The present invention relates to an amplification method of methylated or unmethylated nucleic acid present in a biological sample. Further, the present invention relates to a detection method of methylation and/or unmethylation in a target gene and/or gene locus which is likely be contained in a biological sample, which comprises said amplification method.

This application claims priority from Japanese Patent Application No. 2007-153086, the content of which is incorporated herein by reference.

BACKGROUND ART

A phenomenon that cytosine (C) located in the 5' side of guanine (G) in 5'-CG-3'DNA part (hereinafter referred to as CpG site, or simply as CpG) present in the genome DNA sequence is methylated in mammals has been known. Methylation of CpG is considered to affect the gene expression. Especially, it is believed that CpG may significantly affect the gene expression, if a CpG-rich region (CpG island) is present within a gene promoter region.

Many CpG islands on chromosome are usually protected from methylation. However, once a CpG island within the promoter region is methylated for some reasons, the transcription of the gene is inhibited. For example, if a CpG island within the promoter region in a tumor suppressor gene in a human living body is abnormally methylated and the transcription of that tumor suppressor gene is inactivated, the cell proliferation gets out of control, which allows cell proliferative disorders such as cancers to progress.

Meanwhile, in the region outside the CpG island, cytosine in CpG is usually methylated. However, it has been reported that commonly methylated CpG's cytosines are not methylated in cancers and neoplasms.

With the recent progress of molecular biological approaches, the detection of the presence or absence of DNA methylation has enabled the early detection of cancers and tumors and the monitoring of medical treatment. For example, to rapidly detect methylation in nucleic acids containing CpG, methods for diagnosing cancers and the like through the use of PCR method are disclosed in JP 2000-511776 W (Patent Document No. 1), WO 02/38801 A1 (Patent Document No. 2) and Xiong Z, Laird P W. Nucleic Acids Res. 1997 Jun. 15; 25 (12): 2532-4 (Nonpatent Document No. 1). These methods put emphasis on specifically detecting methylated DNAs.

More particularly, following methods are disclosed: methods by preparing nucleic acid samples from various body fluids, tissues or cell lines, modifying unmethylated cytosine with, for example, bisulfite to be converted to uracil, then (1) amplifying them by PCR method (Methylation-Specific-PCR: MSP method) using a specific primer capable of distinguishing between methylated DNA and unmethylated DNA to detect methylated DNA (Patent Document No. 1) and (2) amplifying them by PCR method using a nonspecific primer incapable of distinguishing between methylated DNA and unmethylated DNA and treating with a restriction enzyme which recognizes difference in the base sequences within the PCR-amplified products to detect the presence or absence and/or the ratio of methylated DNA (Combined Bisulfite Restriction Analysis: COBRA method) (Nonpatent Document No. 1). Detecting the presence of methylated DNA within the base sequence of a particular gene through the use of these methods enables the early detection of cancers and tumors and the monitoring of medical treatment.

Further, a method of detecting methylated DNA and/or unmethylated DNA with a high sensitivity is disclosed (JP 2007-74950 A (Patent Document No. 3)). A method is disclosed wherein after a PCR amplification process, the amplified double-stranded DNA fragments are treated with exonuclease to obtain single-stranded DNA fragments which are detected by DNA microarray.

In MSP and COBRA methods, if a nucleic acid sample (DNA sample) is obtained not from tissues or cell lines but from various body fluids, the subject DNA is often not amplified due to a small amount of the contained DNA.

Usually, it has been known that the sensitivity (probability of obtaining amplified product by PCR method) and the specificity (probability of amplifying the target gene region only) of PCR method itself depend on the base sequence of the primer and the condition of PCR amplification reaction. In order to increase PCR sensitivity, the condition of the PCR amplification process should be loosened, which decreases the specificity of PCR.

MSP method uses primers each having specific sequence for methylated and unmethylated DNAs, respectively, in the amplification process. If the amount of template DNA is small, or if the purity is too low, for example, if various body fluids are used as specimens, the specificity is decreased because the condition of amplification process should be loosened. Therefore, it is hard to know whether the detected amplified product is really amplified from methylated DNA or unmethylated DNA only, and thereby problems arise. Further, there is a big difference between the sequences of a primer specific for unmethylated DNA and a primer specific for methylated DNA (for example, a primer for unmethylated DNA contains more As and Ts, while a primer for methylated DNA will contain more Cs and Gs), so that the amplification sensitivity and specificity may vary between methylated DNA and unmethylated DNA. Further, as the presence or absence of methylation and unmethylation is determined only by the presence or absence of PCR products, the error of the amplification process itself cannot be confirmed.

COBRA method has a problem of its low sensitivity toward methylated DNA. If various body fluids are used as specimens, the detection by COBRA method is likely to be impossible.

Patent Document No. 1: JP 2000-511776 W
Patent Document No. 2: WO 02/38801 A1
Patent Document No. 3: JP 2007-74950 A
Nonpatent Document No. 1: Xiong Z, Laird P W. Nucleic Acids Res. 1997 Jun. 15; 25 (12): 2532-4

DISCLOSURE OF THE INVENTION

Problems to be Solved

The purpose of the present is to provide an amplification method to detect, with a high sensitivity, the presence or absence of methylated or unmethylated nucleic acid of a target gene and/or gene locus in various specimens and a detection method of methylation and/or unmethylation.

Means to Solve the Problems

The present inventors have strenuously studied the subjects described above and have found a detection method, wherein a nonspecific primer capable of amplifying both methylated and unmethylated DNAs and a specific primer capable of amplifying either methylated DNA or unmethylated DNA are designed and amplification reaction is performed to amplify, accurately and with a high sensitivity, the subject DNA, and further methylated and unmethylated nucleic acids are amplified at any proportion by the change of the primer ratio.

Thus, the present invention is composed of the following:
1. An amplification method of CpG-containing nucleic acid derived from a target gene and/or gene locus which is likely be contained in a biological sample, wherein the amplification method comprises a step of amplifying the CpG-containing nucleic acid using a primer set comprising at least a first primer which does not distinguish between methylated and unmethylated nucleic acids and a second primer which distinguishes between methylated and unmethylated nucleic acids, and the second primer has substantially the same primer region as the first primer.
2. The amplification method of nucleic acid according to the preceding aspect 1, wherein the first primer sequence contains at least one CpG site and a base at a position corresponding to cytosine in the CpG site is replaced by a mixed base (Y) and/or mixed base (R) and/or inosinic acid (I).
3. The amplification method of nucleic acid according to the preceding aspect 1 or 2, wherein the second primer sequence contains at least two CpG sites, and the CpG sites are specific to a sequence of methylated nucleic acid or unmethylated nucleic acid.
4. The amplification method of nucleic acid according to any one of the preceding aspects 1 to 3, wherein the amplification is performed by polymerase chain reaction (PCR).
5. The amplification method of nucleic acid according to the preceding aspect 4, further using a third primer which does not distinguish between methylated and unmethylated nucleic acids but has a function of amplifying nucleic acid by making a pair with the first or the second primer.
6. The amplification method of nucleic acid according to any one of the preceding aspects 1 to 5, wherein a concentration ratio of the first primer to the second primer is 10:1 to 1:1.
7. The method according to any one of the preceding aspects 1 to 6, comprising, before said amplification step, a step of treating a biological sample by contacting the biological sample with a reagent for modifying unmethylated cytosine to convert unmethylated cytosine of nucleic acid which can be present in the biological sample, to uracil.
8. A detection method of methylation and/or unmethylation in a target gene and/or gene locus which is likely be contained in a biological sample, comprising the method according to any one of the preceding aspects 1 to 7.
9. The detection method according to the preceding aspect 8, comprising the treatment of the amplified fragment with a restriction enzyme, wherein the restriction enzyme recognizes CG or TG present in the amplified fragment sequence except for the primer region.
10. A primer set comprising at least a first primer which does not distinguish between methylated and unmethylated nucleic acids and a second primer which distinguishes between methylated and unmethylated nucleic acids and which has substantially the same primer region as the first primer.
11. The primer set according to the preceding aspect 10, wherein the primer set is used in the method according to any one of the preceding aspects 1 to 9.
12. A reagent kit comprising the primer set according to the preceding aspect 11.

Effects of Invention

Methylated or unmethylated nucleic acid can be amplified highly accurately by using various specimens according to the amplification method of the present invention. Further, such an amplification method has an advantage of being able to set its sensitivity arbitrarily for methylated or unmethylated nucleic acid. For example, even in the case where the detection of unmethylation is important and the proportion of unmethylated nucleic acid relative to methylated nucleic acid is extremely low, the unmethylated nucleic acid of interest can be accurately amplified according to this method.

Abnormal methylation of nucleic acid can be observed not only in proliferative diseases but also in the other diseases. The present invention is the method which can amplify methylated or unmethylated nucleic acid at any proportion and detect them quantitatively or non-quantitatively by calculation. Therefore, the present method can determine (diagnose) abnormal methylation efficiently and highly accurately and can be used in diagnosis, therapy and prophylaxis of diseases, thus giving a strong impact upon society.

EXPLANATION OF REFERENCES

Figure 1:
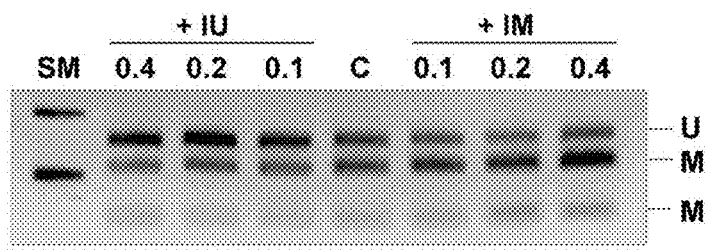
FIG. 1 is a photograph showing the results of Example 2.

SM Size Marker
C Control
IU Primer Specific for Unmethylated DNA
IM Primer Specific for Methylated DNA
U Unmethylated PCR Product
M Methylated PCR Product

DESCRIPTION OF THE PREFERRED EMBODIMENT

The present invention is an amplification method for CpG-containing nucleic acid derived from a gene and/or gene locus which is likely be contained in a biological sample. Further, the present invention is a detection method, comprising such an amplification method, of methylation and/or unmethylation of gene and/or gene locus contained in a biological sample.

In the present invention, "biological sample" means a sample containing nucleic acid prepared from a specimen obtained from a mammal and the like (hereinafter sometimes simply referred to as "sample"). Specimens include the following: various body fluids such as blood, serum, stool, urine, semen, sputum, saliva, nasal discharge, cerebrospinal fluid and tear; or various tissues such as brain, colon, genitourinary organ, lung, kidney, hematopoietic tissue, breast, thymus, testis, ovary and uterine tissue; or cell groups contained therein. Noninvasively obtainable specimens such as stool, sputum and urine are preferred. Further, in the biological samples of the present invention, the purity of DNA may be lower and the amount of contained DNA may be smaller. To obtain a biological sample from a specimen, well known methods per se may be used. DNA can be extracted from a specimen by a well known method per se, for example, by using commercial products such as MagExtractor (from TOYOBO) and QIAamp Stool DNA Isolation Kit (from QIAGEN), or if stool is used as specimens, samples can easily be obtained using a pre-treatment method described in WO 2006/064737.

The obtained biological sample is preferably treated with a reagent to modify all unmethylated cytosines of genes present in a biological sample. An example of such a reagent is bisulfite. Bisulfite treatment converts an unmethylated cytosine to uracil but not methylated cytosine to uracil. Therefore, if cytosine is detected after the treatment, it can be determined that the cytosine is methylated.

Such modification treatment of the unmethylated cytosine can be performed by using a commercially available kit for detecting DNA methylation, for example, DNA methylation Kit, EZ (ZYMO RESEARCH), MethylEasy (Human Genetic Signatures), CpGenome DNA Modification Kit (CHEMICON), and the like.

In the present invention, "a gene and/or gene locus which are likely be contained in a biological sample" refers to various disease-related and microbe-related genes which are likely be contained in a biological sample. For example, causative genes for genetic diseases or the like, cancer tissue-derived genes, indigenous bacteria-derived genes and genes derived from microbes (for example, bacteria and viruses) which are infecting the host from which the sample was collected are included. In particular, gene EPM2AIP (Genbank Accession No. 9852), gene RASSF2A (Genbank Accession No. 9770), gene SFRP2 (Genbank Accession No. 6423), gene Reprimo (Genebank Accession No. 56475) and gene APC (Genbank Accession No. 324) are included.

In the present invention, "CpG-containing nucleic acid" refers to nucleic acids derived from the genes and gene loci described above. CpG-containing nucleic acids may be not only nucleic acids composed of a perfect gene arrangement, but also be fragments such as DNA and RNA fragments as long as nucleic acids comprise regions for amplification. Regions containing CpG include, for example, gene promoter region and 5' region. In particular, the promoter regions of genes EPM2AIP (hMLH1-5' region), RASSF2A, SFRP2, Reprimo and APC are included.

Cytosines in some CpG sites are methylated and some are not. In the present invention, nucleic acid in which the cytosine of interest is methylated is referred to as "methylated nucleic acid" and nucleic acid in which the cytosine of interest is unmethylated as "unmethylated nucleic acid".

The method of the present invention is characterized in that the amplification process is performed using a primer set comprising at least a first primer which does not distinguish between methylated and unmethylated nucleic acids and a second primer which distinguishes between methylated and unmethylated nucleic acids. Further, it is characterized in that the second primer has substantially the same primer region as the first primer. Now, the primer region refers to the region which is a part of the base sequence of CpG-containing nucleic acid within a target gene and/or gene locus and is selected for designing a primer. The length of a primer region, namely the primer size, depends on the type of amplification reaction to be used and, for example, if PCR method is used, the length is between 5 and 40 bp, preferably between 10 and 30 bp.

A primer for use in the present method has a base sequence substantially complementary to the base sequence of a primer region within a template CpG-containing nucleic acid and is composed of an oligonucleotide capable of extending DNA chain from its 3' end. "Substantially complementary" refers to a state in which the base sequence of a primer does not need to be completely complementary to the base sequence of the primer region, but needs to be complementary enough to hybridize the template nucleic acid under the condition of amplification reaction.

"Not distinguish between methylated and unmethylated nucleic acids" in the first primer means that the first primer can hybridize with both methylated and unmethylated nucleic acids nonspecifically under the condition of amplification reaction, and the amplification reaction can be followed. In this specification, a primer having such a function is referred to as "nonspecific primer". The first primer sequence may or may not have a CpG site. When the CpG site is contained, the base complementary to cytosine in the CpG site is preferably replaced by a mixed base (Y) and/or mixed base (R) and/or inosinic acid (I). Meanwhile, the first primer sequence preferably contain at least one CpG site, and the base complementary to cytosine in the CpG site is preferably replaced by a mixed base (Y) and/or mixed base (R) and/or inosinic acid (I).

"Distinguish between methylated and unmethylated nucleic acids" in the second primer means that the second primer may specifically hybridize with either methylated or unmethylated nucleic acid under the condition of amplification reaction, and thus it does not substantially hybridize with the other. In this specification, a primer having such a function is referred to as a "specific primer".

Further, the second primer has substantially the same primer region as the first one. "Substantially the same" does not mean that they are completely identical. The second primer sequence may contain 1 to 8, preferably 1 to 5 base additions and/or deletions, respectively, on the 3' end and/or the 5' end of the first primer sequence. This means that the primer region may be extended and/or shortened. Of course, there may be no need of addition and deletion. More preferably, the sum of the additions and/or deletions on both ends is 5 or less.

Further, the second primer sequence contains 1 to 8, preferably 3 to 6 base differences as compared to the first primer sequence. Such differences include those by base addition and/or deletion on the 3' or the 5' end described above. For example, if the first primer does not contain a CpG site, a CpG site can be contained in the second primer by adding a base (bases). Further, for example, there are times when mixed base (Y) and/or mixed base (R) and/or inosinic acid (I) in the first primer are replaced by cytosine (C) or thymine (T) as in the second primer. In this way, there are times when base difference is found on the overlapping part of the primer regions between the first primer and the second primer. This sequence difference occurs because the first primer is a nonspecific primer, while the second primer is a specific primer. More preferably, the second primer sequence contains at least two CpG sites, and the CpG sites are present specifically in a methylated or unmethylated nucleic acid sequence.

For amplification reaction, a well known method per se can be used. In particular, polymerase chain reaction method (PCR method, Science, 230:1350-1354, 1985), NASBA method (Nucleic Acid Sequence Based Amplification method, Nature, 350, 91-92, 1991) and LAMP method (JP 2001-242169 A) and the like are included, and PCR method can preferably be applied. Further, the design of the primer needs to be changed as appropriate based on the type of amplification reaction, and other primers can be used in addition to the first and the second primers.

For example, when PCR method is used, a third primer can further be used in addition to the first and the second primers. The third primer is one which does not distinguish between methylated and unmethylated nucleic acids, but make a pair with the first or the second primer to perform amplification reaction. In the case of PCR reaction, the amplified product produced with the first or the second primer and the third primer is preferred to be about 100 bp to 300 bp, further preferred to be about 100 bp to 200 bp, but it's needless to say that the size is not limited to them as long as the product can be analyzed by the following detection method. Further, as the primer regions of the first primer and the second primer are substantially the same, the size of the fragment amplified with the first and the third primers and the size of the fragment amplified with the second and the third primers are substantially the same. Namely, the size difference of these amplified fragments is considered to be theoretically 0 to 16 bp, preferably 0 to 10 bp.

Now, as an example using PCR method for amplification reaction, primers for use in the method of the present invention will specifically be explained. Meanwhile, the base sequences of each primer should be referred to Examples.

Regarding the promoter region of gene EPM2AIP (hMLH1-5' region), if the amplification of a methylated nucleic acid is intended, EPM2AIP-F (SEQ ID NO: 1) can be used as the first primer, EPM2AIP-IM (SEQ ID NO: 4) as the second primer, and EPM2AIP-R (SEQ ID NO: 2) as the third primer. Further regarding the same hMLH1-5' region, if the amplification of an unmethylated nucleic acid is intended, EPM2AIP-F (SEQ ID NO: 1) can be used as the first primer, EPM2AIP-IU (SEQ ID NO: 3) as the second primer, and EPM2AIP-R (SEQ ID NO: 2) as the third primer.

Regarding the promoter region of gene RASSF2A, if the amplification of a methylated nucleic acid is intended, RASSF2A-R (SEQ ID NO: 6) can be used as the first primer, RASSF2A-IM (SEQ ID NO: 8) as the second primer, and RASSF2A-F (SEQ ID NO: 5) as the third primer. Further, regarding the same promoter region of gene RASSF2A, if the amplification of an unmethylated nucleic acid is intended, RASSF2A-R (SEQ ID NO: 6) can be used as the first primer, RASSF2A-IU (SEQ ID NO: 7) as the second primer, and RASSF2A-F (SEQ ID NO: 5) as the third primer.

Regarding the promoter region of gene SFRP2, if the amplification of a methylated nucleic acid is intended, SFRP2-F (SEQ ID NO: 9) can be used as the first primer, SFRP2-IM (SEQ ID NO: 11) as the second primer, and SFRP2-R (SEQ ID NO: 10) as the third primer.

Regarding the promoter region of gene Reprimo, if the amplification of a methylated nucleic acid is intended, Rep-R (SEQ ID NO: 13) can be used as the first primer, Rep-IM (SEQ ID NO: 14) as the second primer, and Rep-F (SEQ ID NO: 12) as the third primer.

Regarding the promoter region of gene APC, if the amplification of a methylated nucleic acid is intended, APC-R (SEQ ID NO: 16) can be used as the first primer, APC-IM (SEQ ID NO: 18) as the second primer, and APC-F2 (SEQ ID NO: 17) as the third primer.

Primers for use in the method of the present invention can be prepared using the conventional phosphotriester and phosphodiester methods or any suitable method as in an embodiment in which those methods are automated. In one of such automated embodiments, diethylphosphoramidite is used as a starting material wherein this compound can be synthesized according to a report by Beaucage et al. (Tetrahedron Letters, 22:1859-1862, 1981). A method for synthesizing oligonucleotide on a modified solid support is described in U.S. Pat. No. 4,458,066.

The primers of the present invention include those in which an appropriate label for the detection, for example, fluorescent dye, enzyme, protein, radioisotope, chemiluminescent substance, biotin, or the like is attached to the end of its sequence. As fluorescent dyes for use in the present invention, those which are usually used to label a base to determine and detect nucleic acid can be preferably employed and can include the followings: for example, HEX (4,7,2',4',5',7'-hexachloro-6-carboxyfluorescein, green fluorescent dye), fluorescein, NED (Applied Biosystems, trade name, yellow fluorescent dye), or 6-FAM (Applied Biosystems, trade name, yellow-green fluorescent dye), rhodamine or derivatives thereof (for example, tetramethylrhodamine (TMR)), VIC (Applied Biosystems, trade name, green fluorescent dye) and PET (Applied Biosystems, trade name, red fluorescent dye), but are not limited to them. Among well known labeling methods, an appropriate method can be used as a method of labeling a base with fluorescent dye (see, Nature Biotechnology, 14, p 303-308 (1996)). In addition, commercially available fluorescent labeling kits can also be used (for example, oligonucleotide ECL 3'-oligo labeling system manufactured by Amersham Pharmacia).

A fluorescent substance may be attached to a nonspecific primer, and when amplification reaction is performed by PCR method, fluorescent dye is preferably attached to either the first or the third primer.

When amplification reaction is performed by PCR method in the method of the present invention, specific examples of primers labeled with fluorescent dye will be explained. Examples should be referred to concerning the sequences of primers.

Regarding the promoter region of gene RASSF2A, if the amplification of a methylated nucleic acid is intended, RASSF2A-R (SEQ ID NO: 6) can be used as the first primer, RASSF2A-IM (SEQ ID NO: 8) as the second primer, and RASSF2A-F (SEQ ID NO: 5) as the third primer, and a primer made by attaching 6-FAM to the 5' end of the third primer can be used.

Regarding the promoter region of gene SFRP2, if the amplification of a methylated nucleic acid is intended, SFRP2-F (SEQ ID NO: 9) can be used as the first primer, SFRP2-IM (SEQ. ID. NO: 11) as the second primer, and SFRP2-R (SEQ ID NO: 10) as the third primer, and a primer made by attaching NED to the 5' end of the third primer can be used.

Regarding promoter region of gene Reprimo, if the amplification of a methylated nucleic acid is intended, Rep-R (SEQ ID NO: 13) can be used as the first primer, Rep-IM (SEQ ID NO: 14) as the second primer, and Rep-F (SEQ ID NO: 12) as the third primer, and a primer made by attaching VIC to the 5' end of the first primer can be used.

Regarding the promoter region of gene APC, if the amplification of a methylated nucleic acid is intended, APC-R (SEQ ID NO: 16) can be used as the first primer, APC-IM (SEQ ID NO: 18) as the second primer and APC-F2 (SEQ ID NO: 17) as the third primer, and a primer made by attaching PET to the 5' end of the third primer can be used.

In the present method, an amplified product having the desired ratio and sensitivity can be obtained by changing the concentration ratio of the first primer: the second primer.

The concentration ratio of the first primer: the second primer is preferably 10:1 to 1:1, more preferably 5:1 to 1:1 and more preferably 3:1 to 1:1. The higher the concentration of the second primer becomes, the higher the ratio of amplified product derived from nucleic acid which the second primer can specifically amplify becomes. It is considered that the maximum effect of such second primer can be achieved at the concentration ratio of the first primer to the second primer being 2:1.

In the detection method of the present invention, detecting methylated or unmethylated nucleic acid in a target gene and/or gene locus means detecting the presence or absence of the methylated and/or unmethylated nucleic acid or detecting the ratio between methylated nucleic acid and unmethylated nucleic acid.

The detection method of the present invention comprises (1) the step of determining the presence or absence and/or the amount of methylated DNA and/or unmethylated DNA by treating the amplified product by the amplification method described above with an appropriate restriction enzyme and confirming the size of the fragment by electrophoresis, sequencer or the like or (2) the step of determining the presence or absence and/or the amount of methylated DNA and/or unmethylated DNA by using microarray which is loaded with an oligonucleotide consisting of a sequence complementary to the base sequence of the region in the amplified product except for primer region. According to such a detection method, methylation and/or unmethylation of the region in the amplified product except for the primer region can be detected.

The restriction enzymes for use in detection method comprising a step of treating with a restriction enzyme are preferably those which recognize CG or TG present in the sequence of amplified fragment except for the primer region. Restriction enzyme may be selected depending on the type of gene and the sequence of the amplified product. Treatment conditions such as treatment period with restriction enzyme can be adjusted as needed. Treatment period with restriction enzyme is preferably 5 minutes to 12 hours and more preferably 5 minutes to 15 minutes.

Regarding the promoter region of gene EPM2AIP (hMLH1-5' region), if a primer set of three, EPM2AIP-F (SEQ ID NO: 1), EPM2AIP-R (SEQ ID NO: 2), and EPM2AIP-IM (SEQ ID NO: 4) or EPM2AIP-IU (SEQ ID NO: 3) is used to perform amplification process, restriction enzyme HhaI can be used.

Regarding the promoter region of gene RASSF2A, if a primer set of three, RASSF2A-R (SEQ ID NO: 6), RASSF2A-F (SEQ ID NO: 5), and RASSF2A-IM (SEQ ID NO: 8) or RASSF2A-IU (SEQ ID NO: 7) is used to perform amplification process, restriction enzyme HhaI can be used.

Regarding the promoter region of gene SFRP2, if a primer set of SFRP2-F (SEQ ID NO: 9), SFRP2-IM (SEQ ID NO: 11) and SFRP2-R (SEQ ID NO: 10) is used to perform amplification process, restriction enzyme BssHII can be used.

Regarding the promoter region of gene Reprimo, if a primer set of Rep-R (SEQ ID NO: 13), Rep-IM (SEQ ID NO: 14) and Rep-F (SEQ ID NO: 12) is used to perform amplification process; and regarding the promoter region of gene APC, a primer set of APC-R (SEQ ID NO: 16), APC-IM (SEQ ID NO: 18) and APC-F2 (SEQ ID NO: 17) is used to perform amplification process, restriction enzyme TaqI can be used.

Further, amplified products of multiple genes can simultaneously be treated with a restriction enzyme. If the amplified products of genes RASSF2A and SFRP2 are simultaneously treated with a restriction enzyme, restriction enzyme HhaI can be used. If the amplified products of genes Reprimo and APC are simultaneously treated with a restriction enzyme, restriction enzyme TaqI can be used.

The presence or absence of and/or the amount of methylated DNA and/or unmethylated DNA can be determined by measuring the size of the amplified fragment which has been treated with a restriction enzyme, by electrophoresis. Electrophoresis can be conducted by a well known method per se. Instead of electrophoresis, the size of the fragment can be measured by using a sequencer.

When sequencer is used, those primers labeled with fluorescent dye and the like are preferably used in amplification reaction.

The detection method using a sequencer enables multiple gene regions at the same time, and thus the method is useful. For example, if a sequencer capable of distinguish four types of fluorescent dyes is used, amplification reaction may be performed by attaching each fluorescent dye to respective primers corresponding to four gene regions. Further, primers are required to be designed so as to make a difference in the base length of the amplified products derived from four gene regions. The difference in the base length of amplified products is at least 2 bp, preferably 10 bp or more. The amplified products after the reaction can be simultaneously analyzed by applying to the sequencer.

The further advantages of the detection method using the sequencer are that the reaction time of restriction enzyme and the amount of sample can be considerably cut and reduced.

For example, if determination is conducted without using a sequencer, the treatment time of an amplified product with restriction enzyme depends on the concentration of restriction enzyme, and basically it requires 8 hours or more. Further, in the determination by electrophoresis without using a sequencer, the migration time of 30 minutes or more is required for each gene to be amplified. For example, if determination is conducted by using four genes as markers, as electrophoresis is needed to be carried out for each gene, the required time is 120 minutes (4×30 minutes) or more. Further, when PCR amplification reaction is conducted, at least 5 μL of amplification reaction solution is needed in electrophoresis.

While, if determination is conducted using a sequencer, for sequencer migration, only a small amount of amplification reaction solution is needed in PCR amplification reaction and, for example, 0.02 μL of PCR amplification reaction solution is enough. Since only a small amount of amplification reaction solution is needed in comparison with electrophoresis, 5 to 10 minutes is enough for the treatment with restriction enzyme, when the same amount of restriction enzyme is used. Further, when multiple genes are used as markers, migration can be conducted on the sequencer at the one time. Therefore, four genes can be determined in one sample for 30 minutes (1×30 minutes).

In a method for entrapping amplified product by using a microarray, a substance for detection, for example, fluorescent substance is preferably attached to an oligonucleotide loaded on the microarray.

According to the amplification method described above, if the condition of amplification process is loosened in order to increase the success rate of the amplification process, the specificity of each primer to DNA which is complementary to the primer sequence of interest may be decreased. However, since methylated DNA and/or unmethylated DNA is recognized by the steps (1) and (2) described above, the problem of decreased specificity is solved. Further, in the detection method of the present invention, since the presence or absence of methylated DNA or unmethylated DNA is not determined only by the presence or absence of amplified product, errors in the amplification process can be confirmed. Therefore, the determination of the presence or absence and/or the amount of methylated DNA and/or unmethylated DNA can be more reliably conducted than in conventional examples.

Further, in the present method, in addition to tissue and blood, various body fluids and excreta can be used as specimens.

Since specimens like excreta which can be obtained in a noninvasive way do not require special places for sampling, the present method which can use these specimens is useful because the method can be used for extremely universal purposes including early diagnosis of various cancers.

Therefore, the detection method according to the present invention can provide a convenient and highly accurate determination (diagnosis) of cell proliferative disorders such as cancers by detecting the presence or absence of methylation in a predefined gene and/or gene locus, for example, in a tumor suppressor promoter region of gene. If methylation of DNA can be found in the promoter region of gene, the expression of the gene is inhibited. If this gene is a tumor suppressor gene, the expression of the tumor suppressor gene is inhibited in the living body, and thus cancer is generated and progresses.

With the use of the present method, cell proliferative diseases and/or inflammatory diseases can be examined by detecting methylated and unmethylated nucleic acids of the biological sample described above. The cell proliferative disorders and/or inflammatory diseases described above can be selected from the group comprising low-grade astrocytoma, undifferentiated astrocytoma, glioblastoma, medulloblastoma, pharyngeal cancer, esophageal cancer, gastric cancer, liver cancer, gallbladder cancer, cholangiocarcinoma, pancreas cancer, pancreatitis, small intestine cancer, Crohn's disease, colonic cancer, rectal cancer, ulcerative colitis, lung cancer, renal cancer, leukemia, breast cancer, prostate cancer, endometrial carcinoma and neuroblastoma.

Further, the present invention covers a primer set used in the amplification method and the detection method described above. The primer sets of interest are those comprising at least the first and the second primers, and those further comprising the third primer. Furthermore, a primer necessary for the amplification reaction of the present invention may be included. Meanwhile, these primers may be labeled with a fluorescent dye.

The present invention covers a reagent kit comprising the primer set described above. The reagent kit can comprise other necessary reagents, for example, enzyme and buffer.

EXAMPLE

The present invention will be explained in Examples below, but the present invention is not limited to them.

Example 1

Preparation of DNA Sample

DNA was extracted from normal colon mucosa. CpG region in the promoter region of each gene in DNA extracted from normal colon mucosa is basically unmethylated. Therefore, DNA which had already been identified as being unmethylated was screened from the DNA extracted from normal colon mucosa and referred to as "unmethylated DNA". "Methylated DNA" was obtained by treating this "unmethylated DNA" with SssI methyltransferase.

Each DNA was treated with bisulfite. After the treatment, template-mixed samples were prepared by mixing methylated DNA and unmethylated DNA in various proportions. The template-mixed samples were prepared by adjusting the proportion (%) of methylated DNA to be 100, 50, 10, 5, 1, 0.5, 0.1, 0.05, 0.01 and 0.

Example 2

The sample DNA was amplified by the amplification method of the present invention and the amplified product was subjected to electrophoresis to examine the effects. In the following, the detection method of the present invention using electrophoresis is referred to as Hi-SA method (High-Sensitive Assay).

At first, among the template samples prepared in Example 1, a sample in which the proportion of methylated DNA was 50% (unmethylated DNA: methylated DNA=1:1) was used to examine the effects of "nonspecific primer" in Hi-SA method using the promoter region of gene EPM2AIP (hMLH1-5' region) as a model.

Primers for Hi-SA method, which are capable of amplifying the promoter region of gene EPM2AIP (hMLH1-5' region), are as follows:

```
EPM2AIP-F:
5'-YGGGTAAGTYGTTTTGAYGTAGA      (SEQ ID NO: 1)

EPM2AIP-R:
5'-TATACCTAATCTATCRCCRCCTCA    (SEQ ID NO: 2)

EPM2AIP-IU:
5'-CGGGTAAGTCGTTTTGACGTAGA     (SEQ ID NO: 3)

EPM2AIP-IM:
5'-TGGGTAAGTTGTTTTGATGTAGA     (SEQ ID NO: 4)
```

Primers EPM2AIP-F (SEQ ID NO: 1) and EPM2AIP-R (SEQ ID NO: 2) are nonspecific and designed to hybridize with both DNA having unmethylated cytosine and DNA having methylated cytosine. An amplified product of 150 bp can be obtained with these two primers regardless of the presence or absence of a methylated cytosine.

EPM2AIP-IU (SEQ ID NO: 3) is a primer specific for unmethylated DNA and EPM2AIP-IM (SEQ ID NO: 4) is a primer specific for methylated DNA (hereinafter, a primer specific for unmethylated DNA may be referred to as "IU" and a primer specific for methylated DNA as "IM").

Totally 30 µL of PCR reaction solution was prepared by mixing 15 µL of HotStarTaq (from QIAGEN), 2 µL of sample DNA solution, primers EPM2AIP-F (SEQ ID NO: 1) and EPM2AIP-R (SEQ ID NO: 2), respectively, at 0.4 µM (final concentration) with primer EPM2AIP-IU (SEQ ID NO: 3) or EPM2AIP-IM (SEQ ID NO: 4) at a variety of concentrations, which was then subjected to amplification reaction. The primer EPM2AIP-IU (SEQ ID NO: 3) or EPM2AIP-IM (SEQ ID NO: 4) was added by changing the final concentrations such that the concentrations (µM) would indicate the numbers shown in Table 1 below. Meanwhile, the system described "C" in the Table is one to which neither IU or IM was added.

TABLE 1

| | +IU | | | | +IM | | |
|---|---|---|---|---|---|---|---|
| System | 0.4 | 0.2 | 0.1 | C | 0.1 | 0.2 | 0.4 |
| Content | EPM2A1P-IU Final Concentration 0.4 μM | EPM2A1P-IU Final Concentration 0.2 μM | EPM2A1P-IU Final Concentration 0.1 μM | EPM2AIP-IU or EPM2AIP-IM is not added | EPM2A1P-IM Final Concentration 0.1 μM | EPM2A1P-IM Final Concentration 0.2 μM | EPM2A1P-IM Final Concentration 0.4 μM |

PCR amplification reaction was performed as follows: after a step at 95° C. for 15 minutes, totally 3 cycles: each cycle; 95° C. for 20 seconds, 59° C. for 40 seconds and 72° C. for 20 seconds, then totally 7 cycles: each cycle; 95° C. for 20 seconds, 57° C. for 30 seconds and 72° C. for 20 seconds, then totally 35 cycles: each cycle; 95° C. for 20 seconds, 55° C. for 30 seconds and 72° C. for 20 seconds and finally 72° C. for 7 minutes.

After PCR amplification process, treatment with restriction enzyme HhaI was performed at 37° C. for 12 hours, followed by electrophoresis using 2.5% agarose gel.

The results are shown in FIG. 1. In FIG. 1, SM indicates size marker and each lane indicates each system in Table 1. U indicates the band of unmethylated PCR product, Ms indicate two bands produced by degrading methylated PCR product with restriction enzyme.

Figure 2:
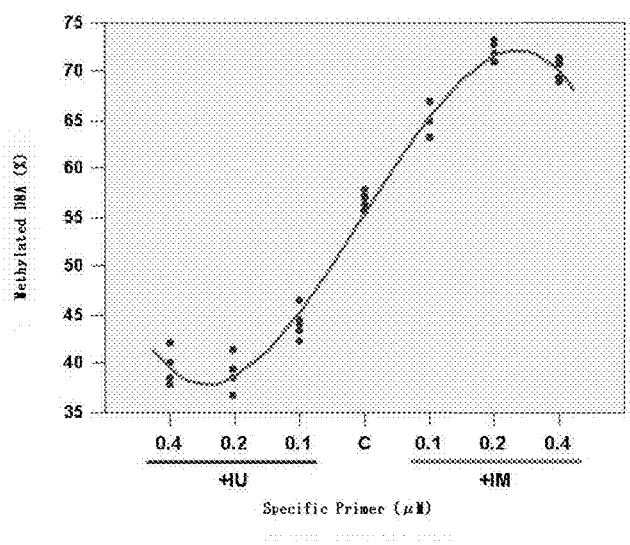
FIG. 2 is a graph exhibiting the ratio of unmethylated PCR products in each system calculated from the results of Example 2.

Further, Hi-SA method was performed for EPM2AIP gene totally six times and the ratio (%) of PCR product not cleaved with restriction enzyme was calculated. In this Example, PCR product not cleaved with restriction enzyme are considered to be amplified from unmethylated DNA as template. These results are shown in FIG. 2 and Table 2. Meanwhile, a product amplified from unmethylated DNA as template is referred to as unmethylated PCR product, and a product amplified from methylated DNA as template as methylated PCR product.

TABLE 2

| | +IU | | | | +IM | | |
|---|---|---|---|---|---|---|---|
| System | 0.4 | 0.2 | 0.1 | C | 0.1 | 0.2 | 0.4 |
| The ratio of unmethylated PCR products (%) (SD) | 60.4 (1.62) | 60.9 (1.52) | 56.8 (1.42) | 43.3 (0.94) | 35.1 (1.89) | 28.1 (0.97) | 29.8 (1.01) |

FIG. 2 shows a graph indicating the relation between the concentrations of specific primers and the detected amounts of detectable unmethylated PCR product and methylated PCR product. It can be realized that the additive effects can be seen below ½ the concentrations of specific primers for detecting methylation and unmethylation relative to the concentrations of nonspecific primers in Hi-SA method, but no effects can be seen at ½ or more.

From the results above, it was found that both methylated and unmethylated DNAs can be amplified at any proportion and detected by changing the ratio of specific primers which recognize either methylated DNA or unmethylated DNA. In addition, it is estimated that the effects of specific primers added can be seen at a concentration ratio of specific primer: nonspecific primer being 1:2. Additive (linear) relation between the concentration of the specific primer and the concentration of PCR product of target methylated DNA or unmethylated DNA was observed until the concentration of specific primer to that of nonspecific primer becomes below ½.

Example 3

Next, primers for Hi-SA method were set for the promoter region of gene RASSF2A in the same manner as in Example 2 (FIG. 3 A), and the effects of IU and IM were examined using a sample with methylated DNA: unmethylated DNA being 1:1. Meanwhile, in FIG. 3A, a gray square at the upper part indicates exons of noncoding region and an arrow above it indicates the transcription initiation part. Vertical lines on the central continuous line indicate each CpG site. Rhomboids above vertical lines indicate recognition sites by restriction enzyme. Thick lines at the lower part indicate PCR product by COBRA or Hi-SA method. Arrows below it indicate IM primer.

Further, COBRA and Hi-SA methods were performed by using nine DNA samples having different mixing ratios prepared in Example 1 to confirm the effects of Hi-SA method.

Example 3-1

Primers for Hi-SA method, which are capable of amplifying the promoter region of gene RASSF2A, are as follows:

```
RASSF2A-F:
5'-TGAAGAGYGAGAGAAAAGAGAGGA      (SEQ ID NO: 5)

RASSF2A-R:
5'-TCCAACCAAACTAAACAAACRATAA     (SEQ ID NO: 6)

RASSF2A-IU:
5'-CCAACCAAACTAAACAAACAATAACCA   (SEQ ID NO: 7)

RASSF2A-IM:
5'-CCAACCAAACTAAACAAACGATAACCG   (SEQ ID NO: 8)
```

RASSF2A-F (SEQ ID NO: 5) and RASSF2A-R (SEQ ID NO: 6) are nonspecific primers and are designed to hybridize with both DNA having methylated cytosine and DNA having unmethylated cytosine, and by using these two primers, an amplified product of 160 bp can be obtained regardless of the presence or absence of a methylated cytosine.

RASSF2A-IU (SEQ ID NO: 7) is designed to hybridize only with DNA having unmethylated cytosine, while RASSF2A-IM (SEQ ID NO: 8) only with DNA having methylated cytosine.

Totally 30 μL of PCR reaction solution was prepared by mixing 15 μL of HotStarTaq (from QIAGEN), 2 μL of sample DNA solution, primers RASSF2A-F (SEQ ID NO: 5) and RASSF2A-R (SEQ ID NO: 6), respectively, at 0.4 μM (final concentration) with primer RASSF2A-IU (SEQ ID NO: 7) or RASSF2A-IM (SEQ ID NO: 8) at a variety of concentrations, which was then subjected to amplification reaction. Primer RASSF2A-IU (SEQ ID NO: 7) or RASSF2A-IM (SEQ ID NO: 8) was added such that the final concentration (μM) would be 0.8, 0.4, 0.2 and 0.1.

PCR amplification reaction was performed as follows: after a step at 95° C. for 15 minutes, totally 3 cycles: each cycle; 95° C. for 20 seconds, 59° C. for 40 seconds and 72° C. for 20 seconds, then totally 7 cycles: each cycle; 95° C. for 20 seconds, 57° C. for 30 seconds and 72° C. for 20 seconds, then totally 35 cycles: each cycle; 95° C. for 20 seconds, 55° C. for 30 seconds and 72° C. for 20 seconds and finally 72° C. for 7 minutes.

Figure 3:
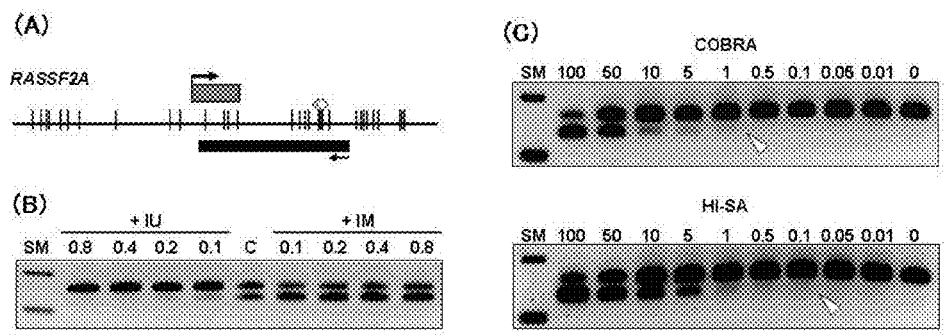
FIG. 3 shows (A) the schematic representation of the promoter region of gene RASSF2A, (B) a photograph showing the result of Example 3-1 and (c) photographs showing the results obtained by COBRA and Hi-SA methods in Example 3-2.

After PCR amplification process, treatment with restriction enzyme HhaI was performed at 37° C. for 12 hours followed by electrophoresis using 3% agarose gel. The results are shown in FIG. 3B. In FIG. 3, SM indicates size marker and each lane indicates the concentrations of added specific primer for methylation or unmethylation (μM). U indicates the band of unmethylated PCR product and Ms indicate two bands produced by degrading methylated PCR product with restriction enzyme. The effect of IU or IM primer was observed as in Example 2.

Example 3-2

Next, COBRA and Hi-SA methods were performed for the promoter region of gene RASSF2A in order to detect methylated DNA. Sensitivities of detecting methylation in COBRA and Hi-SA methods were examined by using nine DNA samples having different mixing ratios prepared in Example 1.

RASSF2A-F (SEQ ID NO: 5) and RASSF2A-R (SEQ ID NO: 6) were used as primers for COBRA method, which are capable of amplifying the promoter region of gene RASSF2A, as in the same manner as in Hi-SA method. In this Example, in order to detect methylated DNA, only RASSF2A-IM (SEQ ID NO: 8), which is a primer specific for methylation, was used as a specific primer in Hi-SA method.

Totally 30 μL of PCR reaction solution containing 15 μL of HotStarTaq (from QIAGEN), each primer, respectively, at 0.4 μM (final concentration), and 2 μL of each DNA sample (prepared in Example 1) was used for amplification reaction of nucleic acid in COBRA method.

Totally 30 μL of PCR reaction solution containing 15 μL of HotStarTaq (from QIAGEN), nonspecific primers respectively at 0.4 μM (at a final concentration), specific primer at 0.2 μM (final concentration), and 2 μL of each DNA sample (prepared in Example 1) was used for amplification reaction of nucleic acid in Hi-SA method.

In both Hi-SA and COBRA methods, amplification reaction was performed as follows: after a step at 95° C. for 15 minutes, totally 3 cycles: each cycle; 95° C. for 20 seconds, 59° C. for 40 seconds and 72° C. for 20 seconds, then totally 7 cycles: each cycle; 95° C. for 20 seconds, 57° C. for 30 seconds and 72° C. for 20 seconds, then totally 35 cycles: each cycle; 95° C. for 20 seconds, 55° C. for 30 seconds and 72° C. for 20 seconds and finally 72° C. for 7 minutes.

After PCR amplification process, treatment with restriction enzyme HhaI was performed at 37° C. for 12 hours followed by electrophoresis using 3% agarose gel.

The results for the promoter region of gene RASSF2A in Hi-SA and COBRA methods are shown in FIG. 3C. In FIG. 3C, SM indicates size marker, each lane number indicates the proportion of methylated DNA (%) in sample DNA. Arrows indicate the degradation products of methylated PCR products.

While the limit of detection of methylation in COBRA method is 1%, the detection of methylation of 0.1% can be achieved in Hi-SA method by using the primer proportion in this Example. In this way, the methylation or unmethylation of the desired DNA can be detected with a high sensitivity in Hi-SA method.

Example 4

Figure 4:
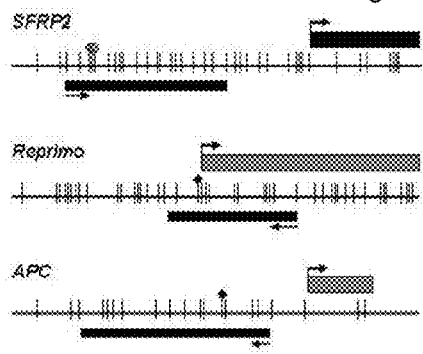
FIG. 4 shows a schematic representation of promoter regions of genes SFRP2, Reprimo and APC.

COBRA and Hi-SA methods were performed for three regions in order to detect methylated DNA in the same manner as in Example 3-2. The examined regions are the promoter regions of genes SFRP2, Reprimo and APC (FIG. 4), which are gene promoter regions reported to be methylated in colon cancer. In FIG. 4, central solid lines indicate each gene. Gray squares at the upper parts indicate exons of noncoding region, a black square at the upper part indicates exons of translation region and arrows above the squares indicate the transcription initiation part. Vertical lines on central solid lines indicate each CpG site. Rhomboids above vertical lines indicate recognition sites by restriction enzyme. Thick lines at the lower parts indicate PCR products by COBRA or Hi-SA method. Arrows below them indicate IM primer.

Sensitivities of detecting methylation in COBRA and Hi-SA methods were examined by using 10 samples prepared in Example 1.

(i) SFRP2 Gene

Primers for COBRA method, which are capable of amplifying the promoter region of gene SFRP2, are as follows:

```
SFRP2-F:
5'-GTYGGAGTTTTTYGGAGTTG       (SEQ ID NO: 9)

SFRP2-R:
5'-ACCCRCTCTCTTCRCTAAATAC    (SEQ ID NO: 10)
```

SFRP2-F (SEQ ID NO: 9) and SFRP2-R (SEQ ID NO: 10) are designed to hybridize with both DNA having methylated cytosine and DNA having unmethylated cytosine. An amplified product of 139 bp can be obtained using these two primers regardless of the presence or absence of a methylated cytosine.

Primers for Hi-SA method, which are capable of amplifying the promoter region of gene SFRP2, are as follows:

```
SFRP2-F:
5'-GTYGGAGTTTTTYGGAGTTG       (SEQ ID NO: 9)

SFRP2-R:
5'-ACCCRCTCTCTTCRCTAAATAC    (SEQ ID NO: 10)

SFRP2-IM:
5'-CGGAGTTTTTCGGAGTTGC        (SEQ ID NO: 11)

SFRP2-F                       (SEQ ID NO: 9)
and

SFRP2-R                       (SEQ ID NO: 10)
``` are nonspecific primers in the same manner as COBRA method and an amplified product of 139 bp can be obtained by using these two primers regardless of the presence or absence of a methylated cytosine.

SFRP2-IM (SEQ ID NO: 11) are designed to hybridize only with DNA having methylated cytosine.

(ii) Reprimo Gene

Primers for COBRA method, which are capable of amplifying the promoter region of gene Reprimo, are as follows:

```
Rep-F:
5'-GGTTTTGTGTTTTATTGYGGAGTG    (SEQ ID NO: 12)

Rep-R:
5'-AAAAATTTCCCAAAAACCTCTCC     (SEQ ID NO: 13)
```

Rep-F (SEQ ID NO: 12) and Rep-R (SEQ ID NO: 13) are designed to hybridize with both DNA having methylated cytosine and DNA having unmethylated cytosine. An amplified product of 138 bp can be obtained with these two primers regardless of the presence or absence of a methylated cytosine.

Primers for Hi-SA method, which are capable of amplifying the promoter region of gene Reprimo, are as follows:

```
Rep-F:
5'-GGTTTTGTGTTTTATTGYGGAGTG       (SEQ ID NO: 12)

Rep-R:
5'-AAAAATTTCCCAAAAACCTCTCC        (SEQ ID NO: 13)

Rep-IM:
5'-AAAAATTTCCCAAAAACCTCTCCGACG    (SEQ ID NO: 14)
```

Rep-F (SEQ ID NO: 12) and Rep-R (SEQ ID NO: 13) are nonspecific primers in the same manner as COBRA method, and an amplified product of 138 bp can be obtained with these two primers regardless of the presence or absence of a methylated cytosine.

Rep-IM (SEQ ID NO: 14) are designed to hybridize only with DNA having methylated cytosine.

(iii) APC Gene

Primers for COBRA method, which are capable of amplifying the promoter region of gene APC, are as follows:

```
APC-F1:
5'-GGTTTTGTGTTTTATTGYGGAGTG    (SEQ ID NO: 15)

APC-R:
5'-CACCAATACAACCACATATCNATCAC  (SEQ ID NO: 16)
```

APC-F1 (SEQ ID NO: 15) and APC-R (SEQ ID NO: 16) are designed to hybridize with both DNA having methylated cytosine and DNA having unmethylated cytosine. An amplified product of 156 bp can be obtained with these two primers regardless of the presence or absence of a methylated cytosine.

Primers for Hi-SA method, which are capable of amplifying the promoter region of gene APC, are as follows:

```
APC-F2:
5'-GGTTTTGTGTTTTATTGNGGAGTG     (SEQ ID NO: 17)

APC-R:
5'-CACCAATACAACCACATATCNATCAC   (SEQ ID NO: 16)

APC-IM:
5'-ACCAATACAACCACATATCGATCACG   (SEQ ID NO: 18)
```

APC-F2 (SEQ ID NO: 17) and APC-R (SEQ ID NO: 16) are nonspecific primers as in the same manner as COBRA method, and an amplified product of 138 bp can be obtained with these two primers regardless of the presence or absence of a methylated cytosine.

APC-IM (SEQ ID NO: 18) are designed to hybridize only with DNA having methylated cytosine. Meanwhile, Ns in the sequences of APC-F2 (SEQ ID NO: 17) and APC-R (SEQ ID NO: 16) are inosinic acids (I).

(iv) Amplification Process

Totally 30 μL of PCR reaction solution containing 15 μL of HotStarTaq (from QIAGEN), each primer at 10 mM (final concentration) and 2 μL of each DNA sample (prepared in Example 1) was used for the amplification reaction of nucleic acid in COBRA method.

Totally 30 μL of PCR reaction solution containing 15 μL of HotStarTaq (from QIAGEN), nonspecific primers, respectively, at 0.4 μM (at a final concentration), specific primer at 0.2 μM (final concentration) and 2 μL of each DNA sample (prepared in Example 1) was used for the amplification reaction of nucleic acid in Hi-SA method.

Together with Hi-SA and COBRA methods, the amplification reaction of gene SFRP2 was performed as follows: after a step at 95° C. for 15 minutes, totally 3 cycles: each cycle; 95° C. for 20 seconds, 58° C. for 40 seconds and 72° C. for 20 seconds, then totally 8 cycles: each cycle; 95° C. for 20 seconds, 56° C. for 30 seconds and 72° C. for 20 seconds, then totally 15 cycles: each cycle; 95° C. for 20 seconds, 54° C. for 30 seconds and 72° C. for 20 seconds, then totally 20 cycles: each cycle; 95° C. for 20 seconds, 52° C. for 30 seconds and 72° C. for 20 seconds and finally 72° C. for 7 minutes.

The amplification reaction of genes Reprimo and APC were performed under the same condition (Example 3) as for RASSF2A, together with Hi-SA and COBRA methods.

After PCR amplification process of both Hi-SA and COBRA methods, the amplified product of SFRP2 was treated with restriction enzyme BssHII (New England Bio Lab) at 50° C. for 12 hours, while amplified products of Reprimo and APC were treated with restriction enzyme TaqI (New England Bio Lab) at 65° C. for 12 hours.

Figure 5:
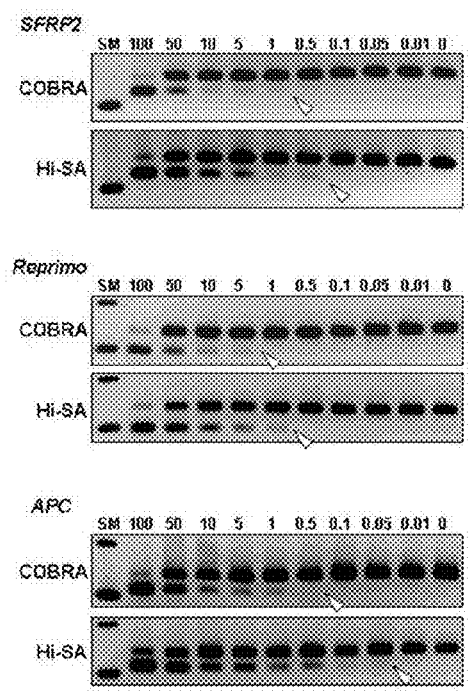
FIG. 5 is photographs showing the results of Example 4.

The results in each region in Hi-SA and COBRA methods are shown in FIG. 5. In FIG. 5, SM indicates size marker, each lane number indicates the proportion of methylated DNA (%) in sample DNAs. Arrows indicate the degradation products of methylated PCR products.

While the limit of detection of methylation in each promoter region of genes SFRP2, Reprimo and APC in COBRA method was between 0.5 and 5%, Hi-SA method exhibited from five- to ten-fold sensitivity over COBRA method. In this way, Hi-SA method enables a highly sensitive detection of the methylation or unmethylation of the desired DNA.

Further, while different types of restriction enzymes were used for each gene (HhaI for gene RASSF2A (Example 3), BssHII for gene SFRP2, TaqI for genes Reprimo and APC), same effects were observed regardless of types of restriction enzymes. From the above, it is predicted that Hi-SA method can be used regardless of the site of gene or gene locus to be amplified and effects of restriction enzyme. That is, Hi-SA method can be used universally. It is considered that the methylation and/or unmethylation of the desired DNA can be detected at any sensitivity by changing the concentrations and the sequence of specific primer.

Example 5

Next, stools obtained from 14 colon cancer patients and those from 14 patients having no neoplasm found in their colons according to colonoscopy were examined as subjects by Hi-SA method using RASSF2A gene as marker.

The modification of nucleic acids of the stool specimens was performed by the method of JP 2006-166712 A (Japanese Patent Application No. 2004-359471) and Hi-SA method was performed by using the resulting samples. Hi-SA method was performed in the same manner as the method of Example 3.

Figure 6:
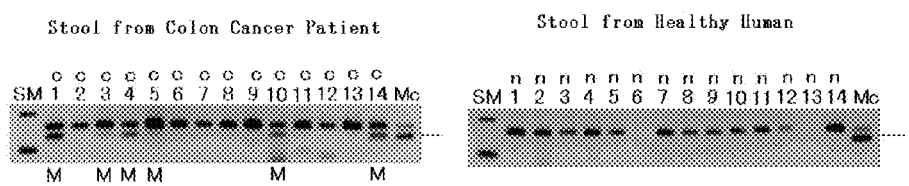
FIG. 6 is photographs showing the results of Example 5.
Figure 7A:
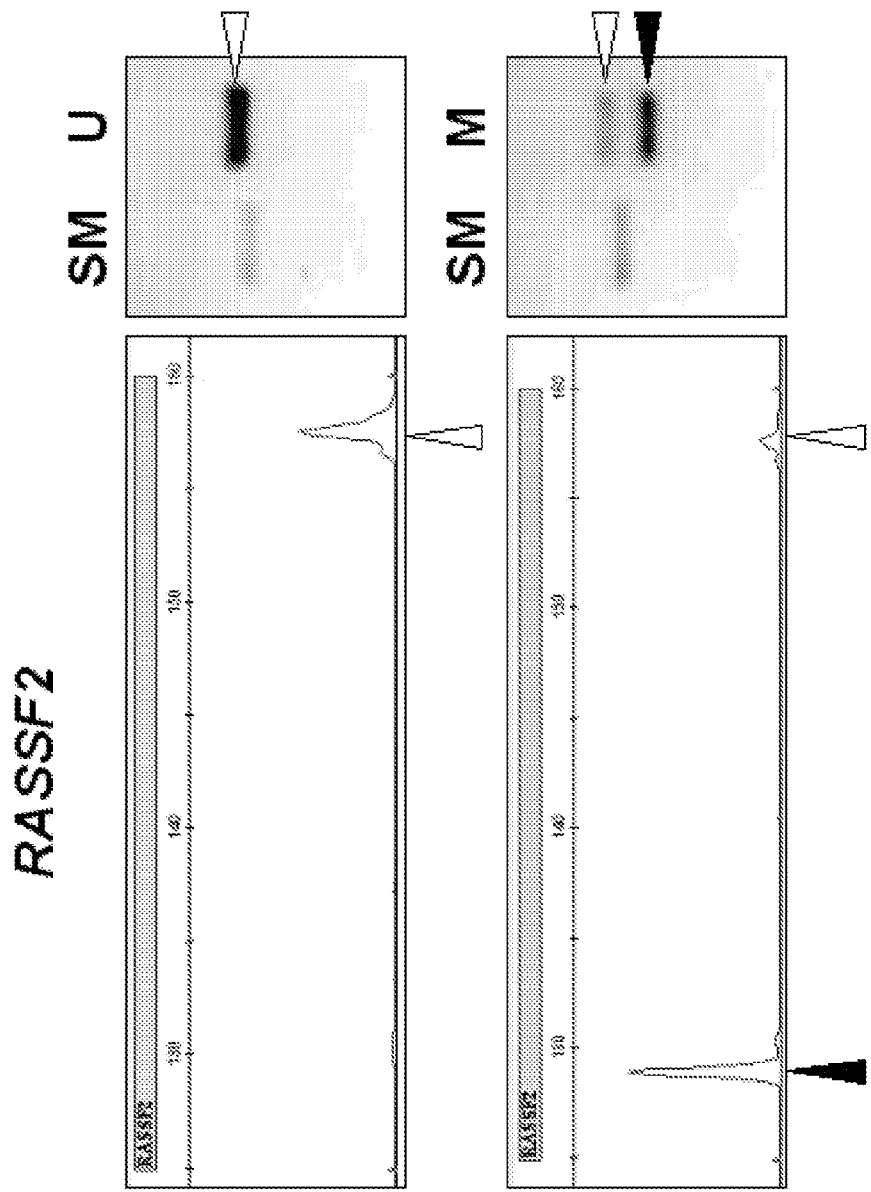
FIGS. 7A-7D show the results of Example 6.
Figure 7B:
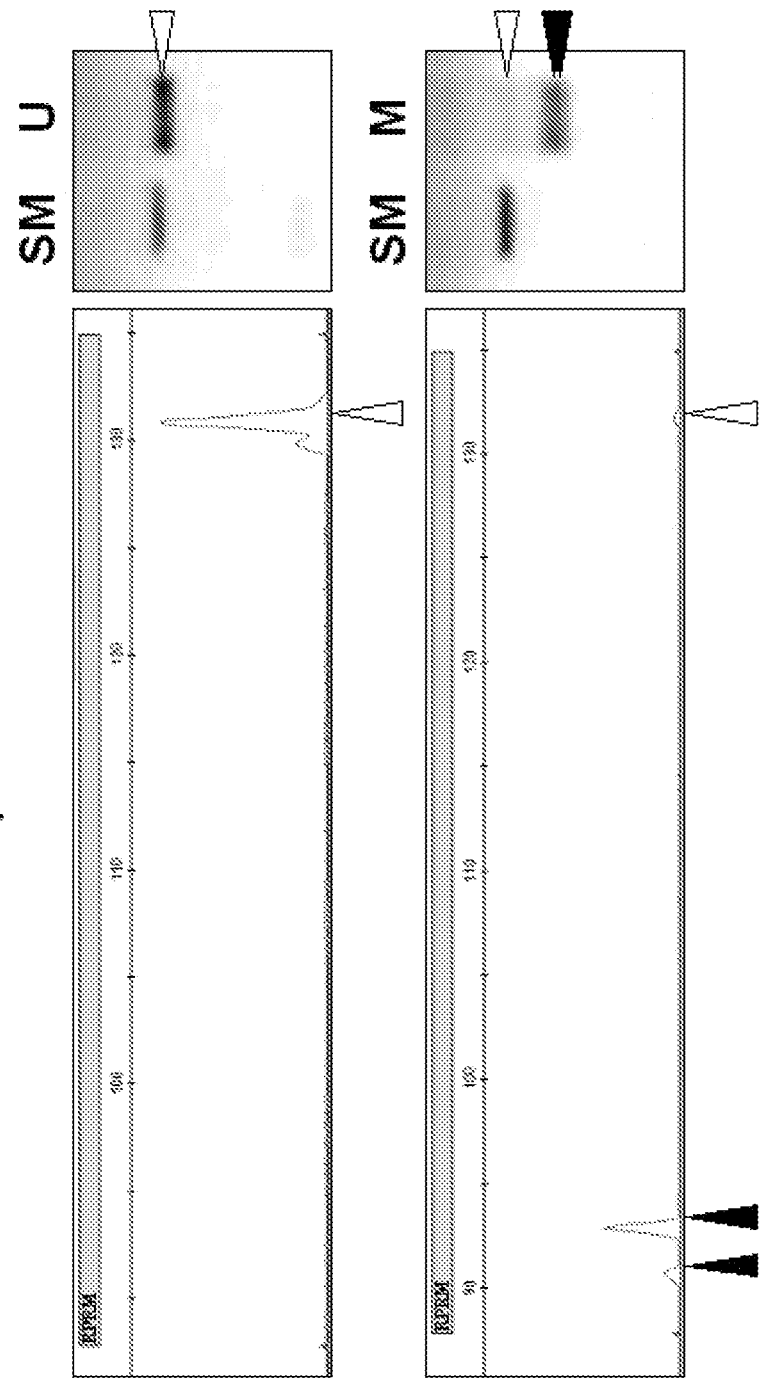
Figure 7C:
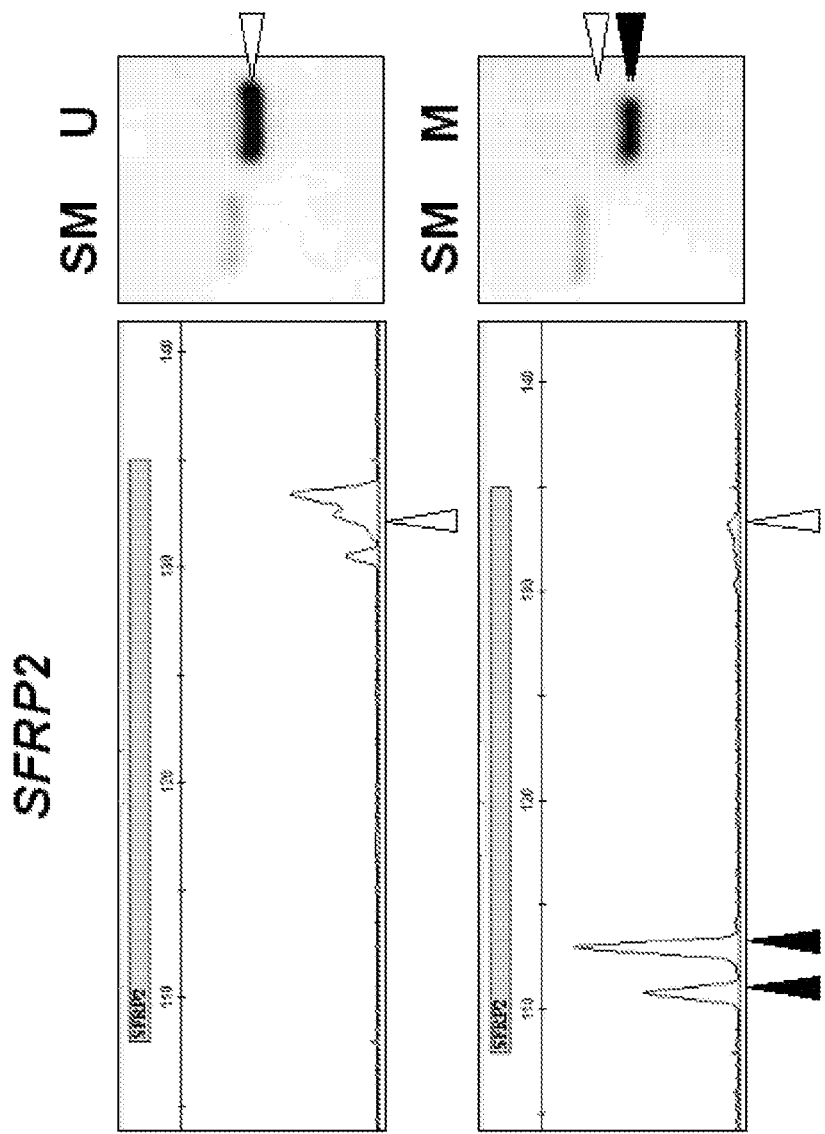
Figure 7D:
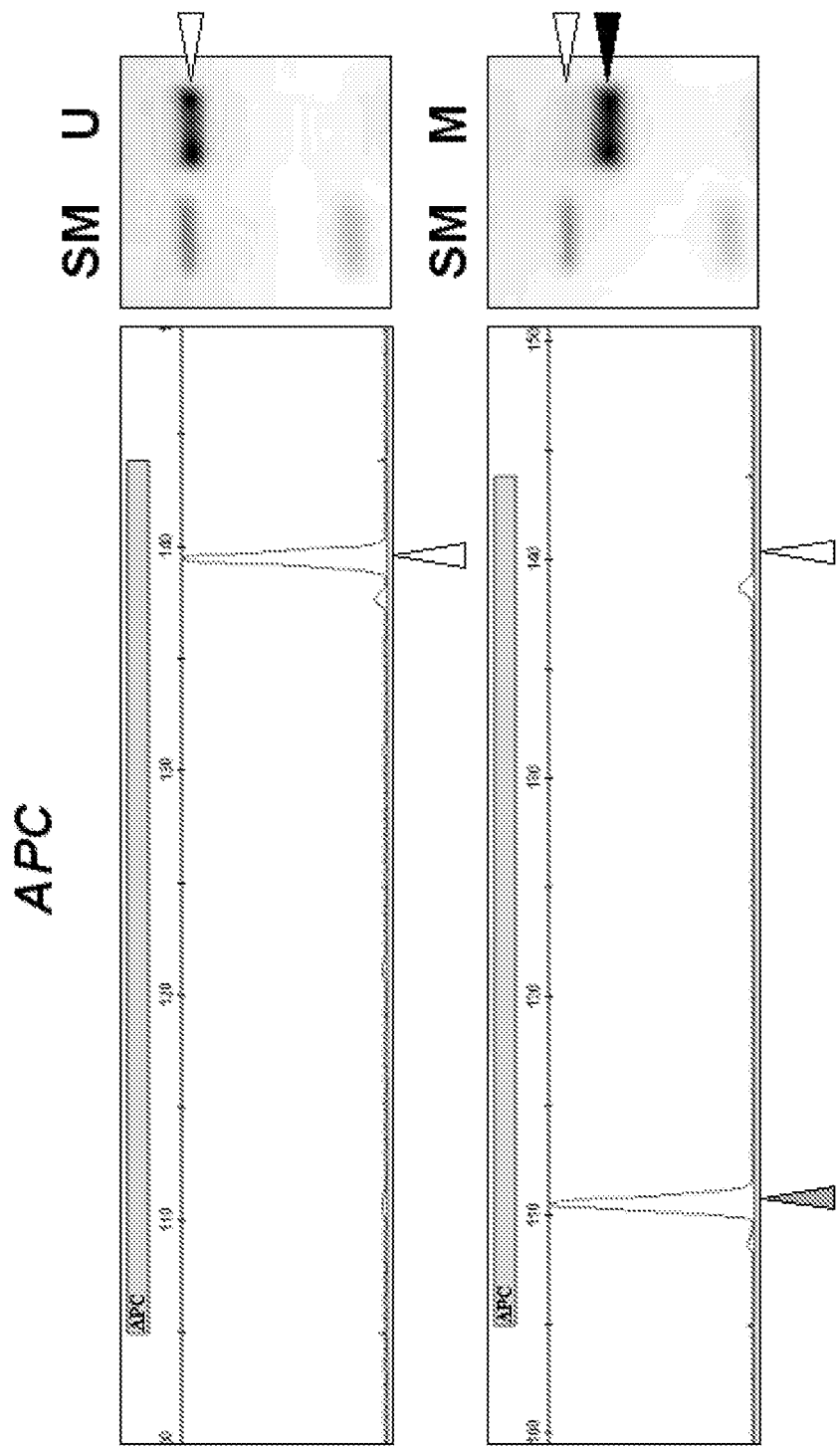
Figure 8A:
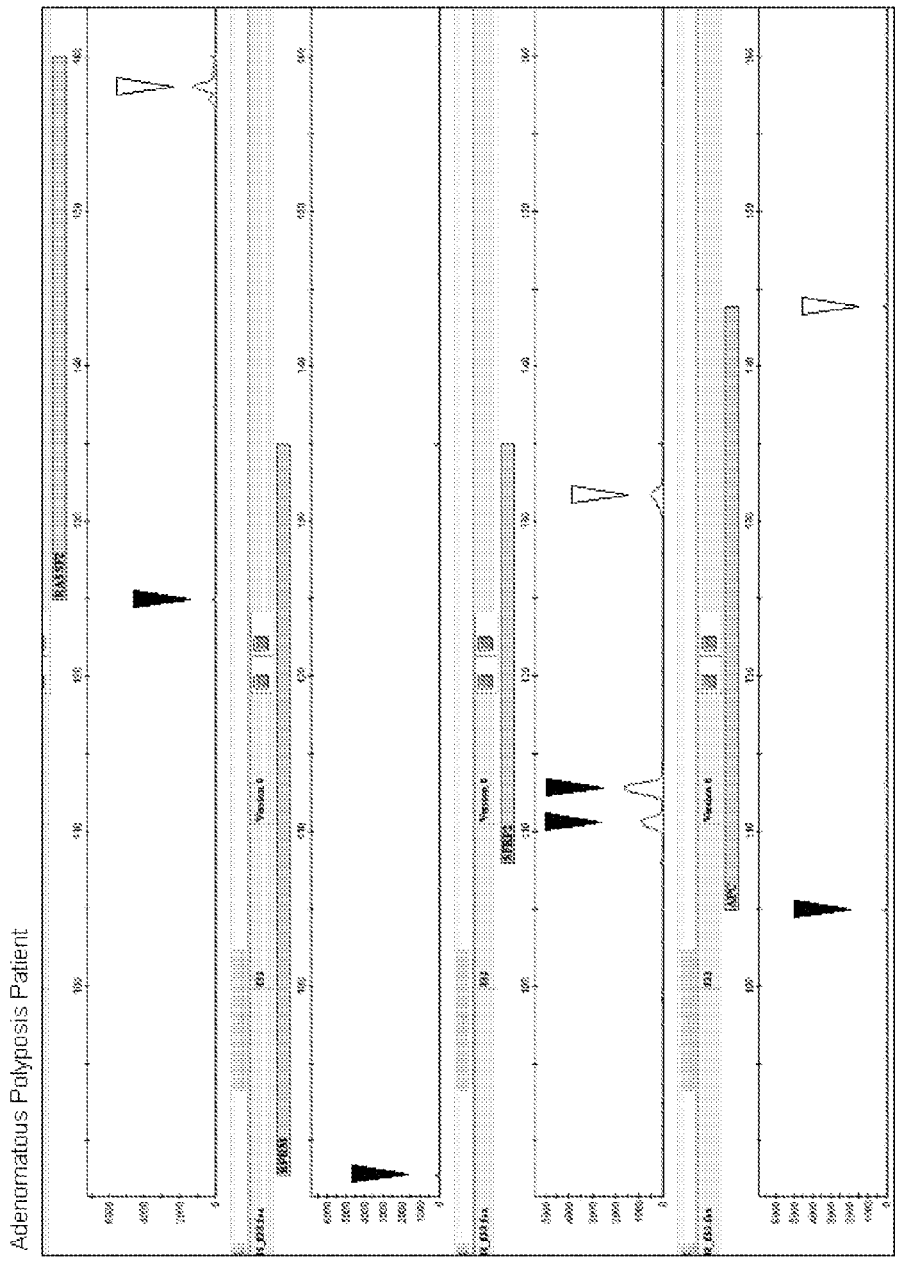
FIGS. 8A-8D show the results of Example 7.
Figure 8B:
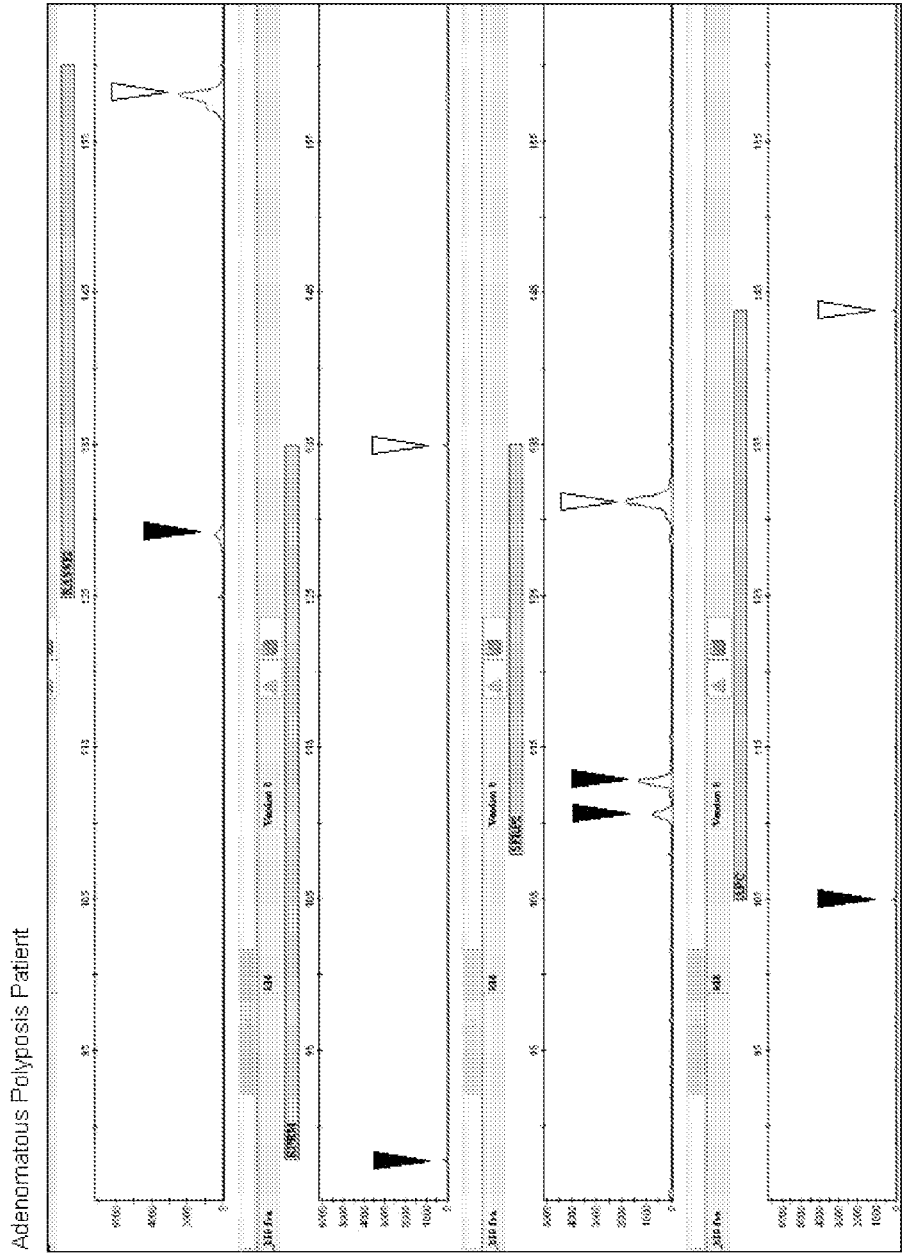
Figure 8C:
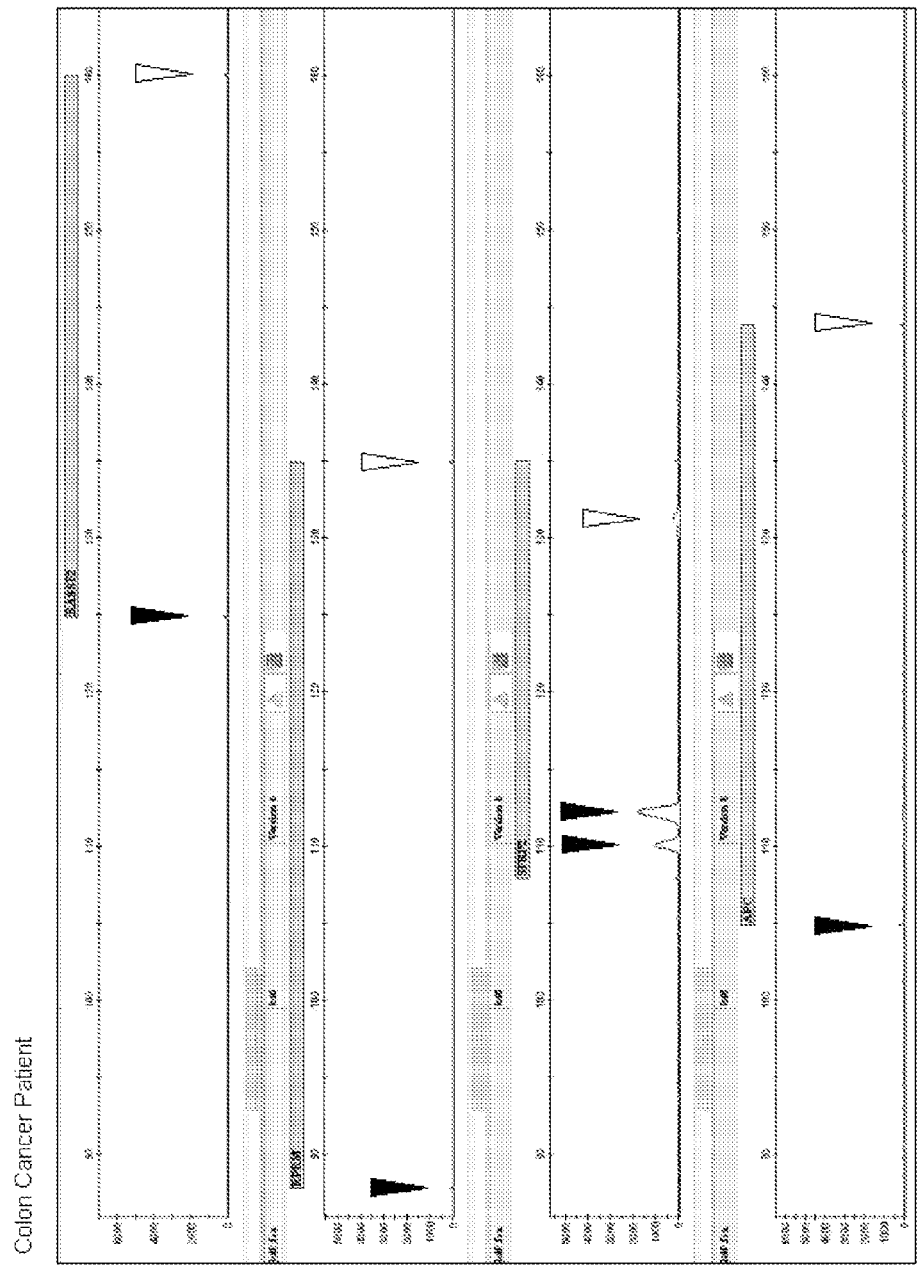
Figure 8D:
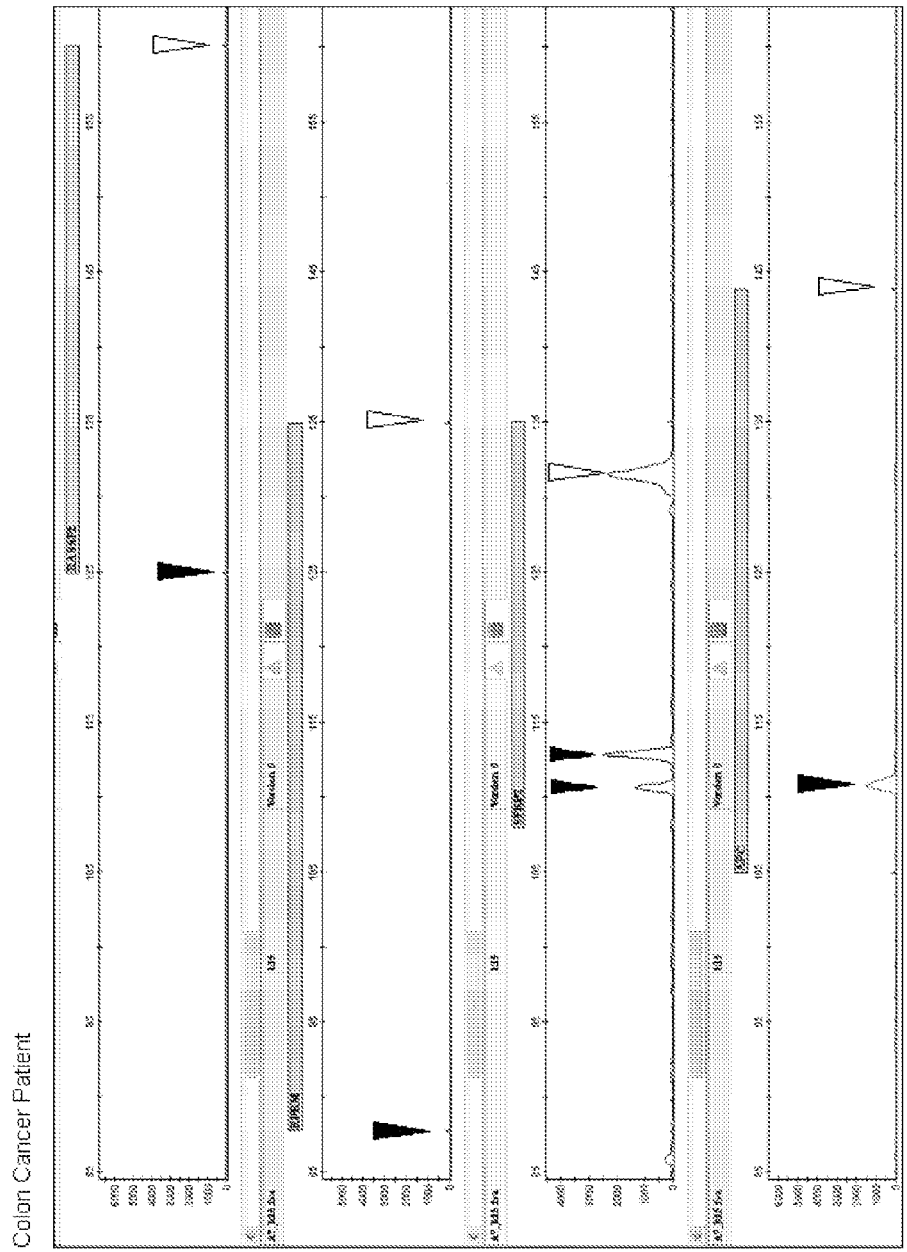

The results are shown in FIG. 6. In FIG. 6, the each lane number indicates sample numbers. SM indicates size marker, arrows indicate the degradation products of methylated PCR products, and Ms indicate methylation detected.

Methylation of RASSF2A gene was detected in 6 of 14 stool specimens from colon patients (43%) and in 0 of 14 stool specimens from healthy subjects (0%).

Example 6

Preparation of DNA Sample

DNA was extracted from normal colon mucosa. CpG region in the promoter region of each gene in DNA extracted from normal colon mucosa is basically unmethylated. Therefore, DNA which had already been identified as unmethylated was screened from the DNA extracted from normal colon mucosa and termed as "unmethylated DNA". "Methylated DNA" was obtained by treating this "unmethylated DNA" with SssI methyltransferase.

Each DNA was treated with bisulfite. After the treatment, samples containing only unmethylated DNA was referred to as U (unmethylated DNA control) and those containing methylated DNA as M (methylated DNA control).

Example 7

Sample DNA was amplified by the amplification method of the present invention and the amplified product was applied to a sequencer to detect whether it was the unmethylated amplified product and/or the methylated amplified product. A primer in which fluorescent substance was attached was used. A method using such fluorescent substance is also referred to as Fluorescent Hi-SA method.

Fluorescent Hi-SA method was performed for genes RASSF2A, SFRP2, Reprimo and APC, used in Examples 3 and 4, by using the samples prepared in Example 6. The following primers in which fluorescent substance was attached were used in each gene region.

(i) RASSF2A Gene

```
RASSF2A-F:
5'-FAM-TGAAGAGYGAGAGAAAAGAGAGGA    (SEQ ID NO: 5)

RASSF2A-R:
5'-TCCAACCAAACTAAACAAACRATAA       (SEQ ID NO: 6)

RASSF2A-IM:
5'-CCAACCAAACTAAACAAACGATAACCG     (SEQ ID NO: 8)
```

(ii) SFRP2 Gene

```
SFRP2-F:
5'-GTYGGAGTTTTTYGGAGTTG            (SEQ ID NO: 9)

SFRP2-R:
5'-NED-ACCCRCTCTCTTCRCTAAATAC      (SEQ ID NO: 10)

SFRP2-IM:
5'-CGGAGTTTTTCGGAGTTGC             (SEQ ID NO: 11)
```

(iii) Reprimo Gene

```
Rep-F:
5'-GGTTTTGTGTTTTATTGYGGAGTG        (SEQ ID NO: 12)

Rep-R:
5'-VIC-AAAAATTTCCCAAAAACCTCTCC     (SEQ ID NO: 13)

Rep-IM:
5'-AAAAATTTCCCAAAAACCTCTCCGACG     (SEQ ID NO: 14)
```

(iv) APC Gene

```
APC-F2:
5'-PET-GGTTTTGTGTTTTATTGNGGAGTG    (SEQ ID NO: 17)

APC-R:
5'-CACCAATACAACCACATATCNATCAC      (SEQ ID NO: 16)

APC-IM:
5'-ACCAATACAACCACATATCGATCACG      (SEQ ID NO: 18)
```

Totally 30 μL of PCR reaction solution containing 15 μL of HotStarTaq (from QIAGEN), nonspecific primers, respectively, at 0.4 μM (at a final concentration), specific primer at 0.2 μM (final concentration) and 2 μL of each DNA sample (prepared in Example 6) was used for amplification reaction of nucleic acid in Fluorescence Hi-SA method. The amplification reaction was performed in the same manner as Example 4.

Each 1 μL of the amplified products of genes RASSF2A and SFRP2 were mixed and treated with restriction enzyme HhaI at 37° C. for 10 hours. Each 1 μL of the amplified products of genes Reprimo and APC were mixed and treated with restriction enzyme TaqI at 65° C. for 10 hours. 1 μL obtained from the process in which each 1 μL of the amplified products of these genes RASSF2A and SFRP2 were mixed and treated with restriction enzyme HhaI, and 1 μL obtained from the process in which each 1 μL of the amplified products of genes Reprimo and APC were mixed and treated with restriction enzyme TaqI, were added with 98 μL of Milli-Q water to a volume of 100 μL, and then 1 μL from that 100 μL solution was applied to a sequencer (ABI 310R Genetic Analyzer). For data acquisition, approximately an hour was needed including preloading time. In order to compare detection sensitivity, electrophoresis for each amplified product (10 μL of PCR reaction solution) was performed by using 3% agarose gel.

The results are shown in FIGS. 7A-7D. The results for genes RASSF2A, SFRP2, Reprimo and APC are shown, respectively. In each region, the upper part shows the results of amplification reaction using control (sample only containing unmethylated DNA) and the lower part shows the results of amplification reaction using methylated DNA. Further, waveforms in the left-hand side are the results from the sequencer and photographs in the right-hand side are the results from electrophoresis. SM indicates size marker, white arrow heads indicate unmethylated PCR products, and gray arrow heads indicate the degradation products of methylated PCR products.

It was found that methylated DNA or unmethylated DNA could be detected with higher sensitivity by Fluorescent Hi-SA method using a sequencer than by Hi-SA method using electrophoresis.

Example 8

Stools obtained from patients with adenomatous polyposis and from colon cancer patients were examined as subject by Hi-SA method using a primer labeled with fluorescent substance. The modification of nucleic acid of the stool specimens was performed by method of JP 2006-166712 A (Japanese Patent Application No. 2004-359471). Fluorescent Hi-SA method was performed in the same manner as the method of Example 7 by using four regions which were described in Example 7 as marker.

The results are shown in FIGS. 8A-8D. Each patient waveform from the above shows the result of genes RASSF2A, Reprimo, SFRP2 and APC, respectively. White arrow heads indicate unmethylated PCR products and gray arrow heads indicate the degradation products of methylated PCR products in each region. From these results, it was found that methylated DNA and unmethylated DNA in stool specimen can be detected with a high sensitivity even by using a sequencer.

INDUSTRIAL APPLICABILITY

As explained above, the method of the present invention can be performed regardless of the site of gene and/or gene locus to be amplified and restriction enzyme. Further, the methylation or unmethylation of the desired nucleic acid can be detected through the arbitrary increase in sensitivity by changing the concentrations of specific primer and sequence. Therefore, according to this method of the present invention, the presence or absence of methylation or unmethylation can be detected accurately and with a high sensitivity, and further the methylated and/or unmethylated nucleic acid can be quantitatively detected.

Further, cancer present in colon can be determined with body specimen, in particular stool specimen, using the detection method of the present invention. The presence or absence of methylation in gene promoter region shown in Examples demonstrated that the presence or absence of methylation in DNA derived from normal mucosal tissue or in DNA derived from colon cancer tissue can be detected through the use of stool by the present method. In this manner, being practically usable as noninvasive DNA material means that the methods described above are not only useful in diagnosis of various diseases, but also useful in applying to various medical examination for colon cancer and the like in healthy population because many specimens can be treated operationally. Further, while it has been known that DNA extraction and purification of stool is difficult, it is considered that the method of the present invention can be applied by using various body specimens besides stool. Therefore, the present method can be applied not only to diagnosis of colon cancer, but also diagnosis of a wide variety of cases, cancers and neoplasms present in respective organs, and further it is considered that those neoplasms can be predicted to some extent.

The invention claimed is:

1. An amplification method of CpG-containing nucleic acid derived from a target gene and/or gene locus which is likely be contained in a biological sample, wherein the amplification method comprises a step of amplifying the CpG-containing nucleic acid using a primer set comprising a first primer which can hybridize with both methylated and unmethylated nucleic acids and a second primer which hybridizes specifically with only one of methylated and unmethylated nucleic acids, wherein the primer region of the second primer contains one to eight base additions and/or deletions on at least one end of the 3' end and 5' end of the primer region of the first primer or does not contain any additions and deletion on the both ends, wherein the first primer and second primer are introduced together and wherein a concentration ratio of the first primer to the second primer is 10:1 to 1:1.

2. The amplification method of nucleic acid according to claim 1, wherein the first primer sequence contains at least one CpG site and a base at a position corresponding to cytosine in the CpG site is replaced by a mixed base (Y) and/or mixed base (R) and/or inosinic acid (I).

3. The amplification method of nucleic acid according to claim 1, wherein the second primer sequence contains at least two CpG sites, and the CpG sites are specific to a sequence of methylated nucleic acid or unmethylated nucleic acid.

4. The amplification method of nucleic acid according to claim 1, wherein the amplification is performed by polymerase chain reaction (PCR).

5. The amplification method of nucleic acid according to claim 4, further using a third primer which does not distinguish between methylated and unmethylated nucleic acids but has a function of amplifying nucleic acid by making a pair with the first or the second primer.

6. The amplification method of nucleic acid according to claim 1, wherein a concentration ratio of the first primer to the second primer is 3:1 to 1:1.

7. The amplification method according to claim 1, comprising, before said amplification step, a step of treating a biological sample by contacting the biological sample with a reagent for modifying unmethylated cytosine to convert unmethylated cytosine of nucleic acid which can be present in the biological sample, to uracil.

8. The amplification method according to claim 1, further comprising treating an amplified fragment with a restriction enzyme, wherein the restriction enzyme recognizes CG or TG present in the amplified fragment sequence except for the primer region.

9. The amplification method according to claim 1, wherein the second primer comprises from one to eight base additions and/or deletions on the 3' end and/or 5" end of the first primer.

10. The amplification method according to claim 5, wherein the target gene is selected from the group consisting of EPM2AIP, RASSF2A, SFRP2, Reprimo and APC.

11. The amplification method according to claim 10, wherein the primers for the EPM2AIP gene, methylated or unmethylated, is selected from the group consisting of EPM2AIP-F (SEQ ID NO: 1), EPM2AIP-IM (SEQ ID NO: 4), EPM2AIP-R (SEQ ID NO: 2) and EPM2AIP-IU (SEQ ID NO: 3) as the second primer, and EPM2AIP-R (SEQ ID NO: 2) as the third primer.

12. The amplification method according to claim 10, wherein the primers for the RASSF2A gene, methylated or unmethylated, is selected from the group consisting of RASSF2A-R (SEQ ID NO: 6), RASSF2A-IM (SEQ ID NO: 8), RASSF2A-F (SEQ ID NO: 5) and RASSF2A-IU (SEQ ID NO: 7).

13. The amplification method according to claim 10, wherein the primers for the SFRP2 gene consists of SFRP2-F (SEQ ID NO: 9), SFRP2-IM (SEQ ID NO: 11) and SFRP2-R (SEQ ID NO: 10).

14. The amplification method according to claim 10, wherein the primers for the Reprimo gene consists of Rep-R (SEQ ID NO: 13), Rep-IM (SEQ ID NO: 14) and Rep-F (SEQ ID NO: 12).

15. The amplification method according to claim 10, wherein the primers for the APC gene consists of APC-R (SEQ ID NO: 16), APC-IM (SEQ ID NO: 18) and APC-F2 (SEQ ID NO: 17).

* * * * *

SEQUENCE LISTING

```
<160> NUMBER OF SEQ ID NOS: 18

<210> SEQ ID NO 1
<211> LENGTH: 23
<212> TYPE: DNA
<213> ORGANISM: Artificial
<220> FEATURE:
<223> OTHER INFORMATION: Designed DNA based on EPM2AIP gene

<400> SEQUENCE: 1
ygggtaagty gttttgaygt aga                                           23

<210> SEQ ID NO 2
<211> LENGTH: 24
<212> TYPE: DNA
<213> ORGANISM: Artificial
<220> FEATURE:
<223> OTHER INFORMATION: Designed DNA based on EPM2AIP gene

<400> SEQUENCE: 2
tatacctaat ctatcrccrc ctca                                          24

<210> SEQ ID NO 3
<211> LENGTH: 23
<212> TYPE: DNA
<213> ORGANISM: Artificial
<220> FEATURE:
<223> OTHER INFORMATION: Designed DNA based on EPM2AIP gene

<400> SEQUENCE: 3
cgggtaagtc gttttgacgt aga                                           23

<210> SEQ ID NO 4
<211> LENGTH: 23
<212> TYPE: DNA
<213> ORGANISM: Artificial
<220> FEATURE:
<223> OTHER INFORMATION: Designed DNA based on EPM2AIP gene
```

<400> SEQUENCE: 4
tgggtaagtt gttttgatgt aga   23

<210> SEQ ID NO 5
<211> LENGTH: 24
<212> TYPE: DNA
<213> ORGANISM: Artificial
<220> FEATURE:
<223> OTHER INFORMATION: Designed DNA based on RASSF2A gene

<400> SEQUENCE: 5
tgaagagyga gagaaaagag agga   24

<210> SEQ ID NO 6
<211> LENGTH: 25
<212> TYPE: DNA
<213> ORGANISM: Artificial
<220> FEATURE:
<223> OTHER INFORMATION: Designed DNA based on RASSF2A gene

<400> SEQUENCE: 6
tccaaccaaa ctaaacaaac rataa   25

<210> SEQ ID NO 7
<211> LENGTH: 27
<212> TYPE: DNA
<213> ORGANISM: Artificial
<220> FEATURE:
<223> OTHER INFORMATION: Designed DNA based on RASSF2A gene

<400> SEQUENCE: 7
ccaaccaaac taaacaaaca ataacca   27

<210> SEQ ID NO 8
<211> LENGTH: 27
<212> TYPE: DNA
<213> ORGANISM: Artificial
<220> FEATURE:
<223> OTHER INFORMATION: Designed DNA based on RASSF2A gene

<400> SEQUENCE: 8
ccaaccaaac taaacaaacg ataaccg   27

<210> SEQ ID NO 9
<211> LENGTH: 20
<212> TYPE: DNA
<213> ORGANISM: Artificial
<220> FEATURE:
<223> OTHER INFORMATION: Designed DNA based on SFRP2 gene

<400> SEQUENCE: 9
gtyggagttt ttyggagttg   20

<210> SEQ ID NO 10
<211> LENGTH: 22
<212> TYPE: DNA
<213> ORGANISM: Artificial
<220> FEATURE:
<223> OTHER INFORMATION: Designed DNA based on SFRP2 gene

<400> SEQUENCE: 10
acccrctctc ttcrctaaat ac   22

<210> SEQ ID NO 11
<211> LENGTH: 19
<212> TYPE: DNA

```
<213> ORGANISM: Artificial
<220> FEATURE:
<223> OTHER INFORMATION: Designed DNA based on SFRP2 gene

<400> SEQUENCE: 11
cggagttttt cggagttgc                                                  19

<210> SEQ ID NO 12
<211> LENGTH: 24
<212> TYPE: DNA
<213> ORGANISM: Artificial
<220> FEATURE:
<223> OTHER INFORMATION: Designed DNA based on Reprimo gene

<400> SEQUENCE: 12
ggttttgtgt tttattgygg agtg                                            24

<210> SEQ ID NO 13
<211> LENGTH: 23
<212> TYPE: DNA
<213> ORGANISM: Artificial
<220> FEATURE:
<223> OTHER INFORMATION: Designed DNA based on Reprimo gene

<400> SEQUENCE: 13
aaaaatttcc caaaaacctc tcc                                             23

<210> SEQ ID NO 14
<211> LENGTH: 27
<212> TYPE: DNA
<213> ORGANISM: Artificial
<220> FEATURE:
<223> OTHER INFORMATION: Designed DNA based on Reprimo gene

<400> SEQUENCE: 14
aaaaatttcc caaaaacctc tccgacg                                         27

<210> SEQ ID NO 15
<211> LENGTH: 24
<212> TYPE: DNA
<213> ORGANISM: Artificial
<220> FEATURE:
<223> OTHER INFORMATION: Designed DNA based on APC gene

<400> SEQUENCE: 15
ggttttgtgt tttattgygg agtg                                            24

<210> SEQ ID NO 16
<211> LENGTH: 26
<212> TYPE: DNA
<213> ORGANISM: Artificial
<220> FEATURE:
<223> OTHER INFORMATION: Designed DNA based on APC gene
<220> FEATURE:
<221> NAME/KEY: misc_feature
<222> LOCATION: (21)..(21)
<223> OTHER INFORMATION: n stands for inosinic acid

<400> SEQUENCE: 16
caccaataca accacatatc natcac                                          26

<210> SEQ ID NO 17
<211> LENGTH: 24
<212> TYPE: DNA
<213> ORGANISM: Artificial
<220> FEATURE:
<223> OTHER INFORMATION: Designed DNA based on APC gene
<220> FEATURE:
```

```
<221> NAME/KEY: misc_feature
<222> LOCATION: (18)..(18)
<223> OTHER INFORMATION: n stands for inosinic acid

<400> SEQUENCE: 17
ggttttgtgt tttattgngg agtg                                          24

<210> SEQ ID NO 18
<211> LENGTH: 26
<212> TYPE: DNA
<213> ORGANISM: Artificial
<220> FEATURE:
<223> OTHER INFORMATION: Designed DNA based on APC gene

<400> SEQUENCE: 18
accaatacaa ccacatatcg atcacg                                        26
```